(12) United States Patent
Abbasi

(10) Patent No.: US 11,633,205 B1
(45) Date of Patent: Apr. 25, 2023

(54) LATERAL DISC CUTTER WITH REPLACEABLE BLADES

(71) Applicant: Advance Research System, LLC, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 526 days.

(21) Appl. No.: 16/784,638

(22) Filed: Feb. 7, 2020

Related U.S. Application Data

(63) Continuation-in-part of application No. 16/052,535, filed on Aug. 1, 2018, now Pat. No. 11,160,577.

(60) Provisional application No. 62/539,797, filed on Aug. 1, 2017.

(51) Int. Cl.
| | | |
|---|---|---|
| A61B 17/32 | (2006.01) | |
| A61B 17/16 | (2006.01) | |
| A61B 17/3207 | (2006.01) | |
| A61F 2/44 | (2006.01) | |
| A61B 17/00 | (2006.01) | |

(Continued)

(52) U.S. Cl.
CPC .... *A61B 17/32002* (2013.01); *A61B 17/1671* (2013.01); *A61B 17/1617* (2013.01); *A61B 17/320725* (2013.01); *A61B 2017/00261* (2013.01); *A61B 2017/320024* (2013.01); *A61B 2017/320028* (2013.01); *A61B 2017/320775* (2013.01); *B23B 51/101* (2013.01); *Y10T 82/12* (2015.01); *Y10T 408/8588* (2015.01)

(58) Field of Classification Search
CPC ....... A61B 2017/320028; A61B 2017/320024; A61B 2017/320775; A61B 2017/00261; A61B 17/1671; A61B 17/1659; A61B 17/1617; A61B 17/00234; A61B 17/1615; A61B 17/32002; A61B 17/320725; A61B 17/320016; A61B 17/1662; A61B 17/16; A61F 2/4455; A61F 2/46; Y10T 408/8588; Y10T 408/858; Y10T 408/85; Y10T 82/12; B23B 2250/04; B23B 51/101; B23D 77/04; B23C 2260/04; B23C 3/12; B23C 5/00
USPC .......... 606/79–85, 86 R, 167, 170, 171, 174; 408/152, 158, 181, 182, 183
See application file for complete search history.

(56) References Cited

U.S. PATENT DOCUMENTS

| | | |
|---|---|---|
| 6,224,604 B1 | 5/2001 | Suddaby |
| 6,726,690 B2 | 4/2004 | Eckman |

(Continued)

*Primary Examiner* — Marcela I. Shirsat
(74) *Attorney, Agent, or Firm* — Christensen, Fonder, Dardi & Herbert PLLC; Stuart J. Olstad

(57) ABSTRACT

A lateral disc cutter for morcellating and decorticating tissue of an intervertebral disc from between adjacent vertebrae. The device can be arranged in a retracted configuration for insertion via an access tube, and in an extended configuration for cutting of tissue in the target region. The blades may be extended to contact the concave endplate in an orientation that is substantially parallel to a mid-plane of the intervertebral disc. Blades of the device may be configured with a convex profile that substantially conforms to the concave shape of the endplate for enhanced contact length between the blade and the endplate. In some embodiments, the blades are configured for removal and replacement without need for tools, with the blades selectively determining a maximum displacement width of the morecellator assembly.

12 Claims, 13 Drawing Sheets

(51) Int. Cl.
 *A61F 2/46* (2006.01)
 *B23B 51/10* (2006.01)

(56) References Cited

U.S. PATENT DOCUMENTS

| | | | |
|---|---|---|---|
| 6,840,944 B2 * | 1/2005 | Suddaby | A61B 17/1671 606/105 |
| 6,902,568 B2 * | 6/2005 | Serhan | A61B 17/1617 606/79 |
| 7,329,267 B2 | 2/2008 | Weber | |
| 8,034,088 B2 | 10/2011 | Pagano | |
| 8,480,675 B2 | 7/2013 | Betts | |
| 8,551,097 B2 | 10/2013 | Schmitz et al. | |
| 8,568,416 B2 | 10/2013 | Schmitz et al. | |
| 8,579,902 B2 | 11/2013 | Bleich et al. | |
| 8,585,704 B2 | 11/2013 | Schmitz et al. | |
| 8,652,138 B2 | 2/2014 | Bleich et al. | |
| 8,663,228 B2 | 3/2014 | Schmitz et al. | |
| 8,845,639 B2 | 9/2014 | Wallace et al. | |
| 8,894,652 B2 | 11/2014 | Seifert et al. | |
| 9,247,952 B2 | 2/2016 | Bleich et al. | |
| 9,314,253 B2 | 4/2016 | Mimran et al. | |
| 9,320,618 B2 | 4/2016 | Schmitz et al. | |
| 9,326,777 B2 | 5/2016 | Tally | |
| 9,345,491 B2 | 5/2016 | Bleich et al. | |
| 9,351,741 B2 | 5/2016 | Schmitz et al. | |
| 9,456,829 B2 | 10/2016 | Saadat et al. | |
| 9,463,029 B2 | 10/2016 | Schmitz et al. | |
| 9,463,041 B2 | 10/2016 | Bleich et al. | |
| 2003/0135218 A1 | 7/2003 | Eckman | |
| 2003/0220650 A1 | 11/2003 | Major et al. | |
| 2004/0122457 A1 | 6/2004 | Weber | |
| 2006/0116690 A1 | 6/2006 | Pagano | |
| 2008/0249552 A1 | 10/2008 | Eliachar et al. | |
| 2011/0015635 A1 * | 1/2011 | Aryan | A61B 17/1671 606/84 |
| 2015/0173917 A1 | 6/2015 | Radcliffe et al. | |
| 2015/0306348 A1 | 10/2015 | Wallace et al. | |
| 2016/0030060 A1 | 2/2016 | Tally et al. | |
| 2017/0014142 A1 | 1/2017 | Schmitz et al. | |

* cited by examiner

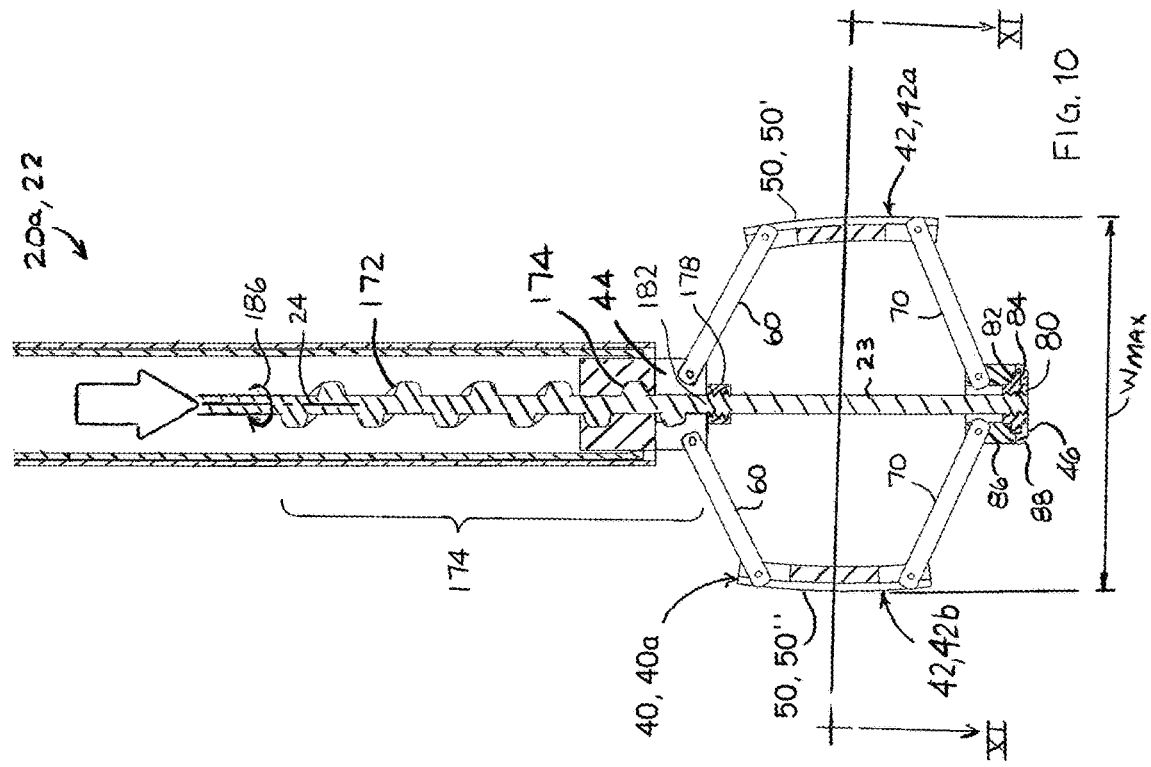
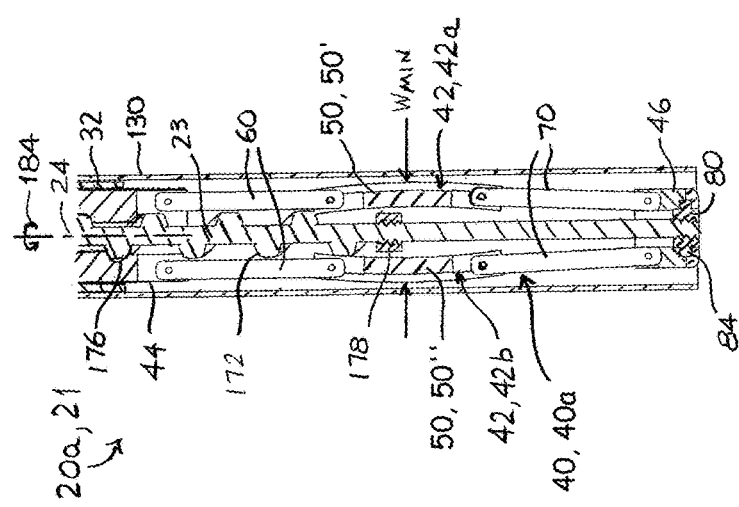
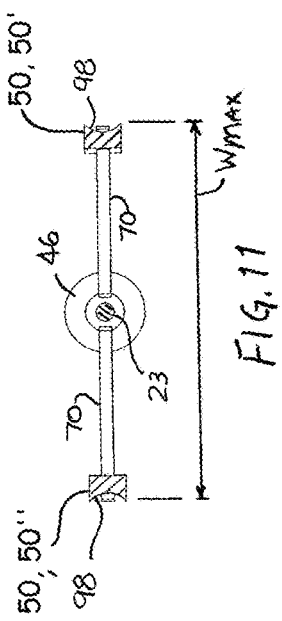

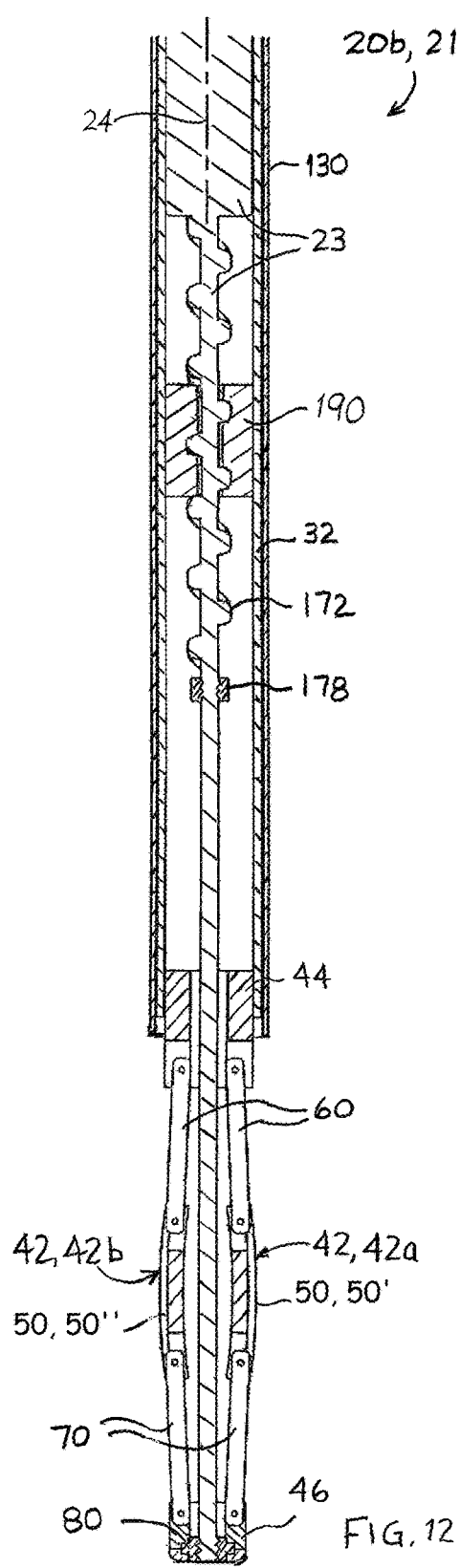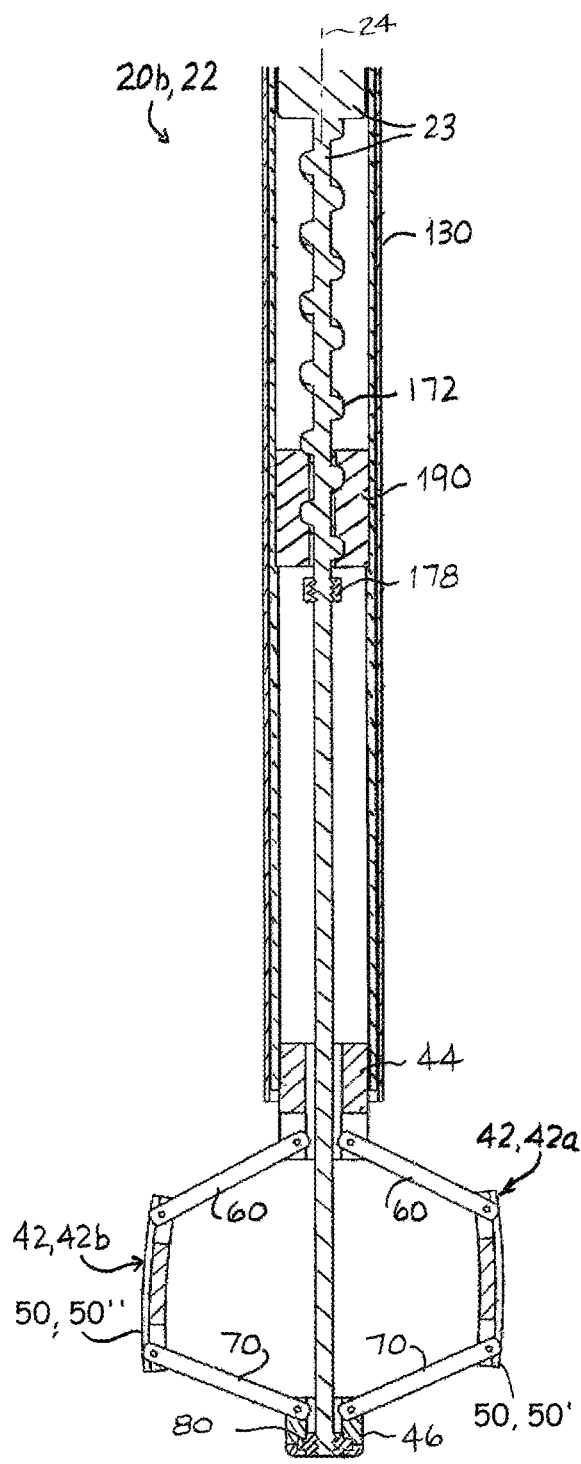

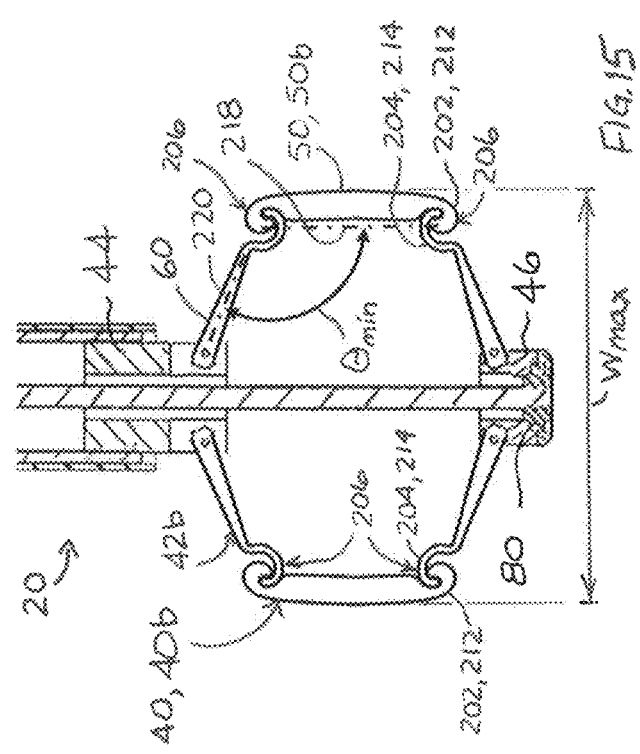
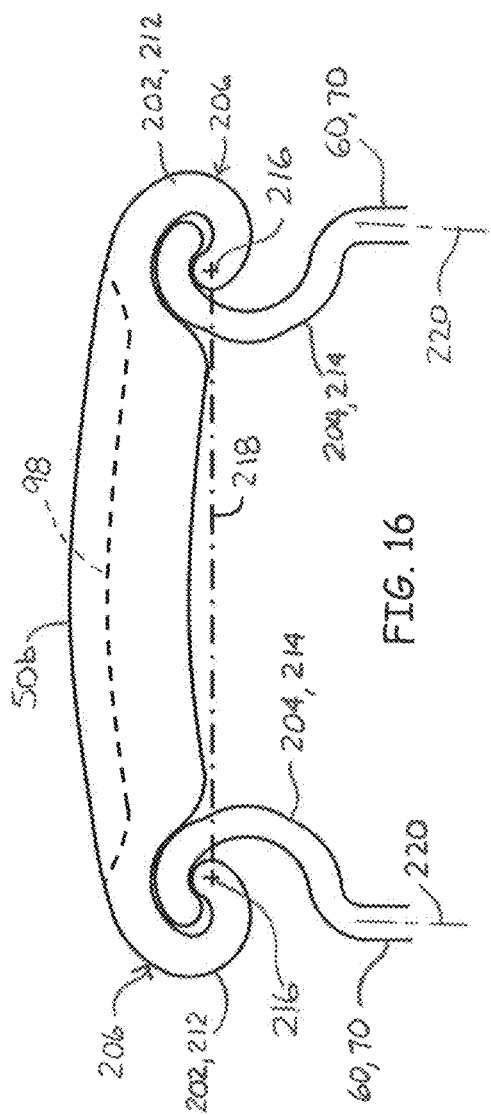
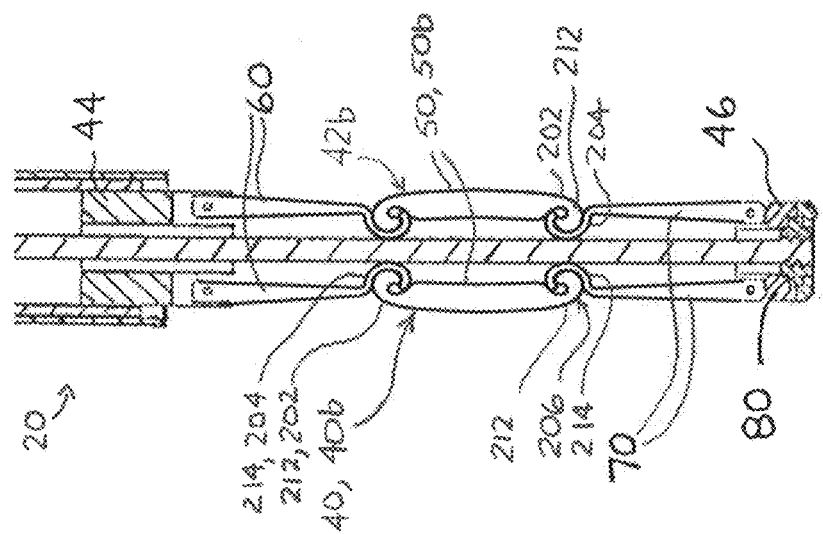

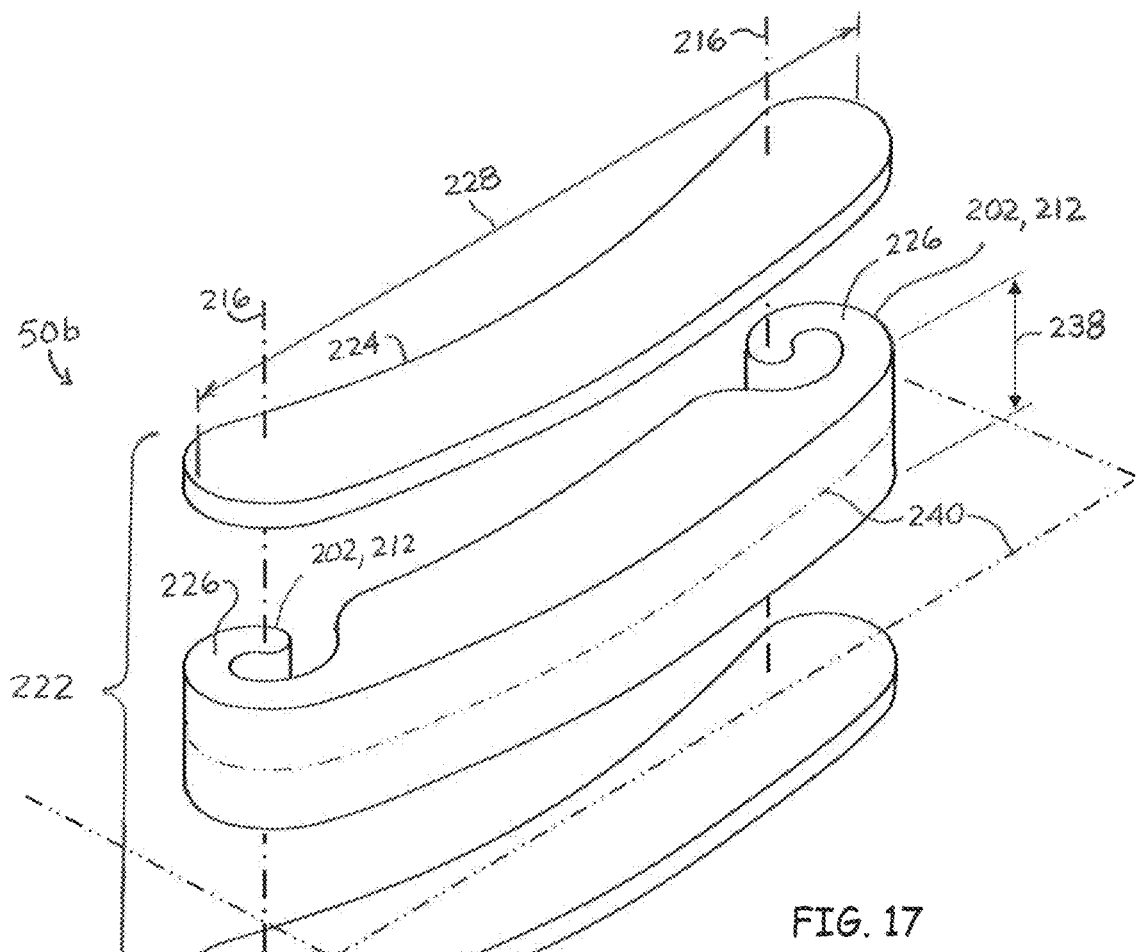
FIG. 17
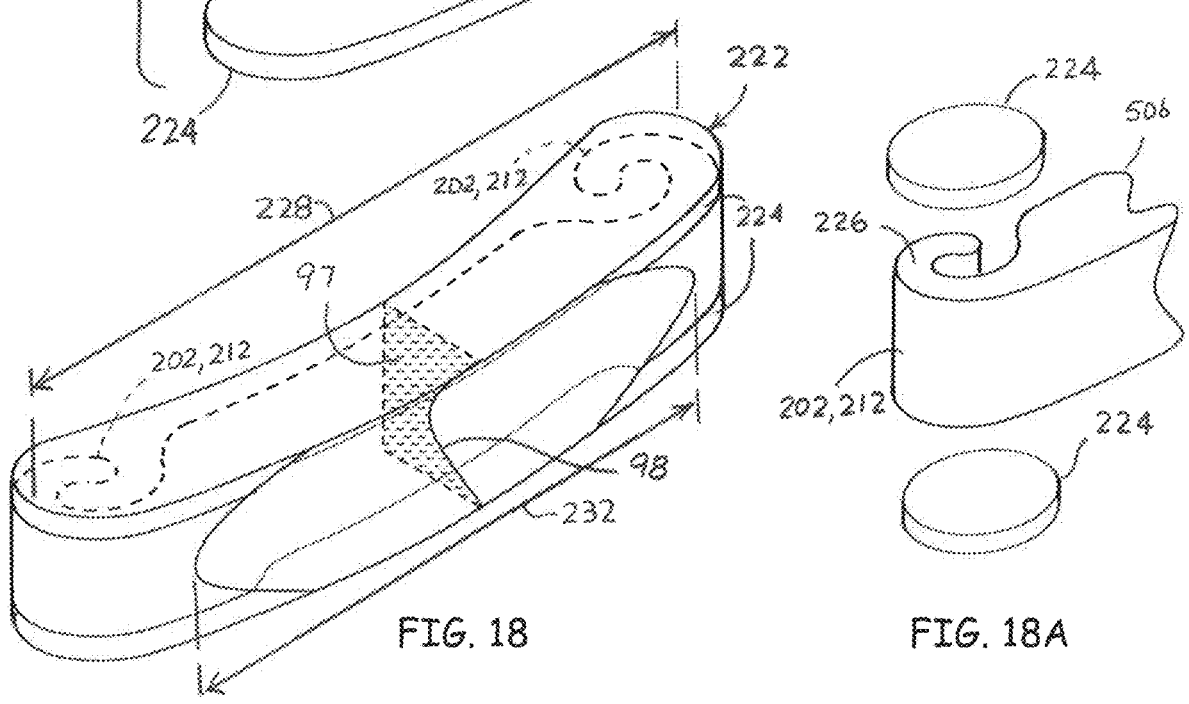
FIG. 18
FIG. 18A

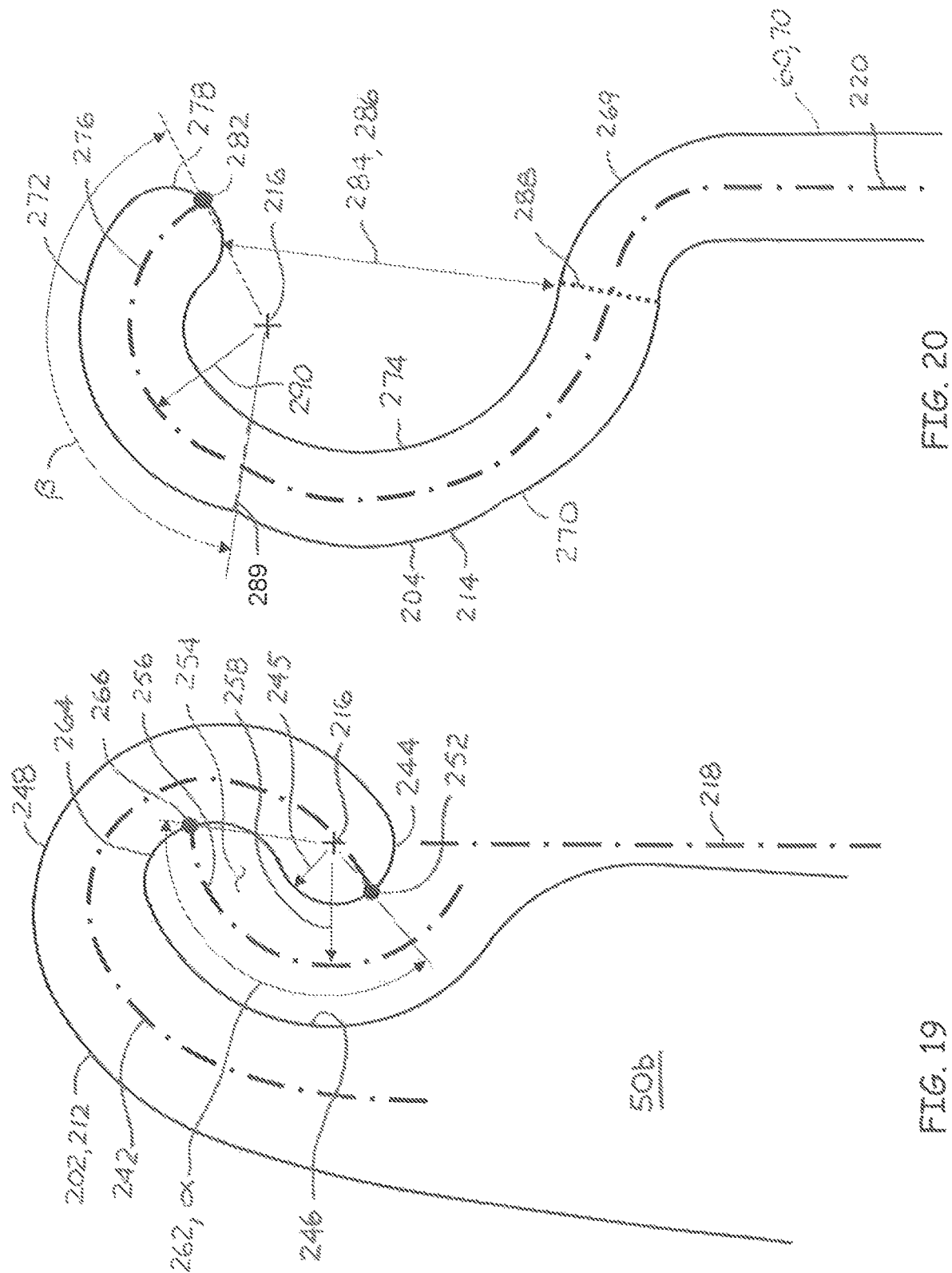

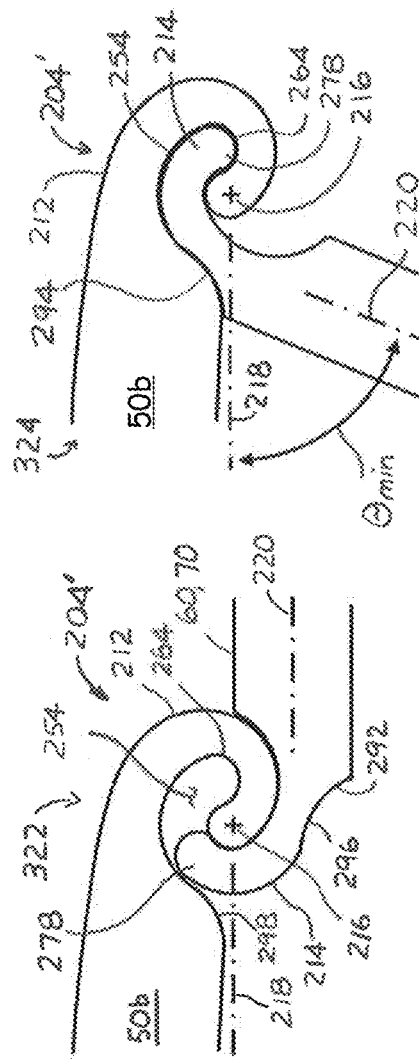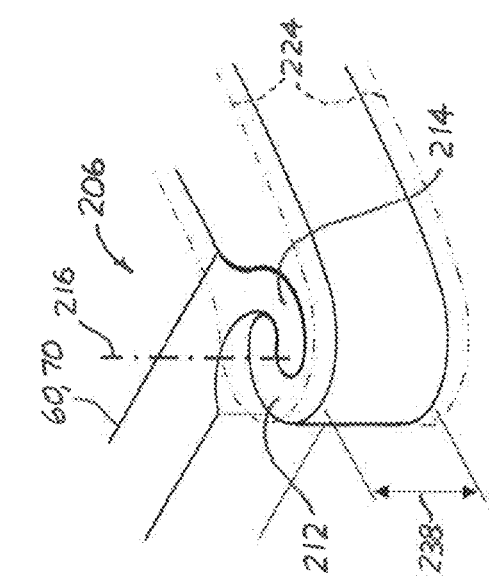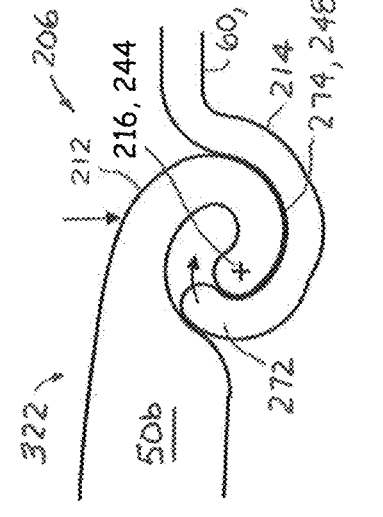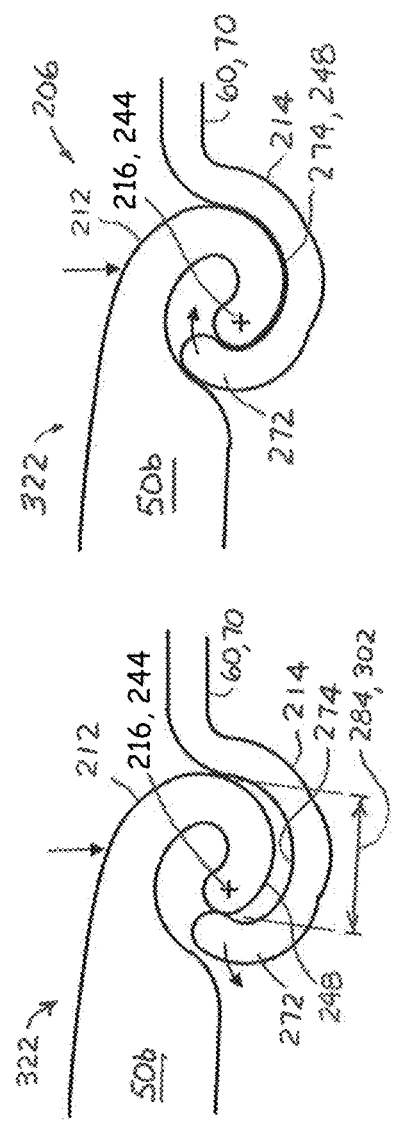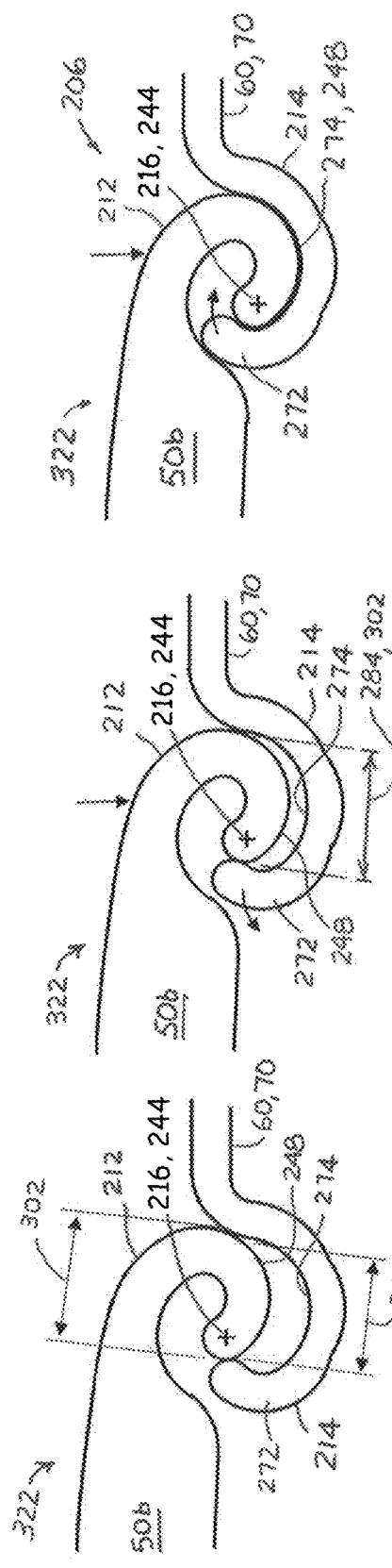

LATERAL DISC CUTTER WITH REPLACEABLE BLADES

RELATED APPLICATIONS

This application is a continuation-in-part of U.S. patent application Ser. No. 16/052,535, filed Aug. 1, 2018, which claims the benefit of U.S. Provisional Patent Application No. 62/539,797, filed Aug. 1, 2017, the disclosures of which are hereby incorporated by reference herein in their entirety.

FIELD OF THE DISCLOSURE

The disclosure relates generally to surgical instruments and techniques for treatment of the spine, and more specifically to tools and techniques for morcellation and decortication of disc tissue.

BACKGROUND

Techniques for the fusion of adjacent spinal vertebrae often involve promoting the growth of bony tissue between the endplates of the adjacent vertebrae. Growth of bony tissue is best facilitated by removing the tissue of the intervertebral disc that is in contact with the end plates, so that a clear path between adjacent endplates, and filling the resulting space with bone growth promoters, such as bone graft material (in addition to other spinal fusion appurtenances, such as fusion cages). The bone growth promoter typically extends between and contacts the endplates. The greater the exposed surface area of the vertebral endplates prior to implanting the bone growth promoter, the better.

Removing bone tissue from and between the endplates for satisfactory exposure of the endplate bone can be a time consuming process. As with all surgical procedures, reducing the time required to perform a surgical step is at a premium. An apparatus and technique that reduces the decortication and morcellation of intervertebral discs in spinal fusion procedures would be welcomed.

SUMMARY

Various embodiments of the disclosure provide a mechanism that orient one or more morcellating blades to remain substantially parallel to a mid-plane of the intervertebral disc as the mechanism extends the blade(s) in the superior/inferior direction and into contact with a vertebral endplate. Accordingly, the blades are oriented for enhanced contact relative to morcellating blades of the prior art. In some embodiments, the blades of the device are configured with a convex profile that substantially conforms to the concave shape of the endplate for enhanced contact between the blade and the endplate during decortication of the intervertebral disc.

Conventional disc cutters for morcellating intervertebral discs tend to fan radially outward from a pivot point close to a central axis of the access tube. Such conventional disc cutters provide a cutting edge that contacts the vertebral endpoints along an inherently limited span. Accordingly, conventional disc cutters require several passes of the blade to sufficiently prepare the intervertebral space for spinal fusion procedures. The lateral disc cutter of the present disclosure increases the line of contact between the blade and the vertebral endplate, thus requiring fewer scraping passes to properly prepare the vertebral endplate.

Various embodiments of the disclosure include cutter assemblies having linkages and blades with end structures that rotate about each other to provide structural rigidity through the range of articulation. In some embodiments, the end structures become seated together to define the articulation angle at which the span of the morcellator assembly is maximum. The seating of the end structures further enhances the structural rigidity of the cutter assembly. In some embodiments, a kit provides a plurality of blades with structural variations that may be utilized to select a desired maximum span of the morcellator assembly.

BRIEF DESCRIPTION OF THE DRAWINGS

FIG. 1A is an enlarged view of cutter assemblies at a distal end of the lateral disc cutter in the retracted configuration of FIG. 1;

FIG. 2A is an enlarged view of cutter assemblies at a distal end of the lateral disc cutter in the fully extended configuration of FIG. 2;

FIG. 9 is a partial sectional view of a screw driven lateral disc cutter in a retracted configuration according to an embodiment of the disclosure;

FIG. 10 is a sectional view of the screw driven lateral disc cutter of FIG. 9 in an extended configuration according to an embodiment of the disclosure;

FIG. 11 is a sectional view of a morcellator assembly at plane XI-XI of FIG. 10 according to an embodiment of the disclosure;

FIG. 12 is a sectional view of a screw driven lateral disc cutter with drive threads contained in a sleeve of the lateral disc cutter in a retracted configuration according to an embodiment of the disclosure;

FIG. 13 is a sectional view of the screw driven lateral disc cutter of FIG. 12 in an extended configuration according to an embodiment of the disclosure;

FIG. 14 is a partial sectional view of a lateral disc cutter with a morcellator assembly in a retracted configuration that utilizes spiral-shaped and hook-shaped structures for pivoting connection of the blades according to an embodiment of the disclosure;

FIG. 15 is a partial sectional view of a lateral disc cutter with the morcellator assembly of FIG. 14 in an extended configuration according to an embodiment of the disclosure;

FIG. 16 is an enlarged, partial view of a cutter assembly in a partially extended configuration with blades having spiral-shaped structures according to an embodiment of the disclosure;

FIG. 17 is an exploded view of a blank blade assembly with spiral-shaped end structures according to an embodiment of the disclosure;

FIG. 18 is an assembled view of the blade assembly of FIG. 17 with a concave cutting cross-section according to an embodiment of the disclosure;

FIG. 18A is a partially exploded view of an alternative blank blade assembly with spiral-shaped end structures according to an embodiment of the disclosure;

FIG. 19 is an enlarged plan view of a spiral-shaped blade end structure according to an embodiment of the disclosure;

FIG. 20 is an enlarged plan view of a hook-shaped linkage end structure according to an embodiment of the disclosure;

FIG. 21 is an enlarged perspective view of a pivot structure with cooperating spiral-shaped and hook-shaped structures according to an embodiment of the disclosure;

FIG. 22A is a plan view of the pivot structure of FIG. 21 in an in-line orientation according to an embodiment of the disclosure;

FIG. 22B is a plan view of the pivot structure of FIG. 21 in fully articulated orientation according to an embodiment of the disclosure;

FIGS. 23A through 23C are plan views of cooperating spiral-shaped and hook-shaped structures being snappingly assembled according to an embodiment of the disclosure;

DETAILED DESCRIPTION OF THE FIGURES

Figure 1:
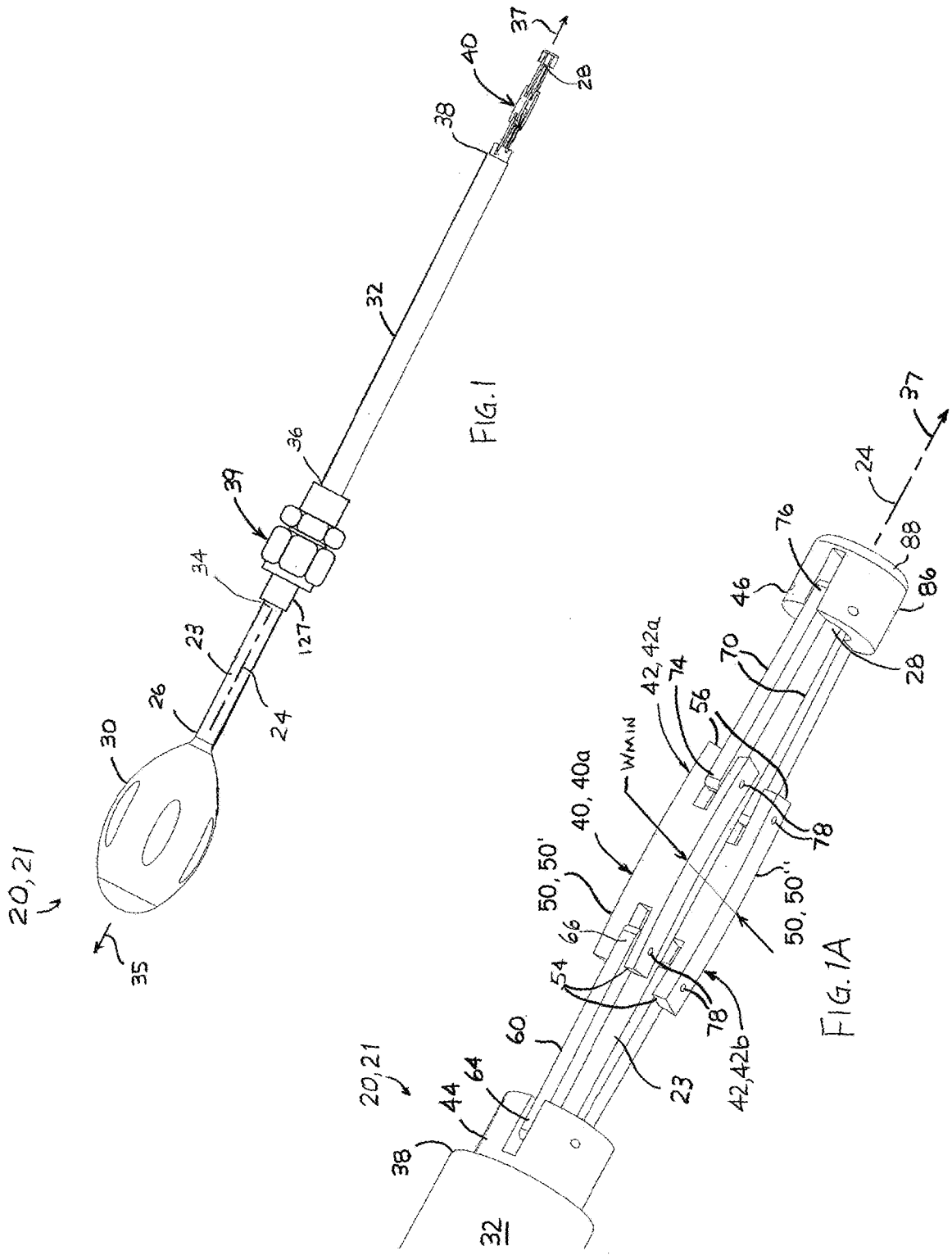
FIG. 1 is a perspective view of a lateral disc cutter in a retracted configuration according to an embodiment of the disclosure.
Figure 2:
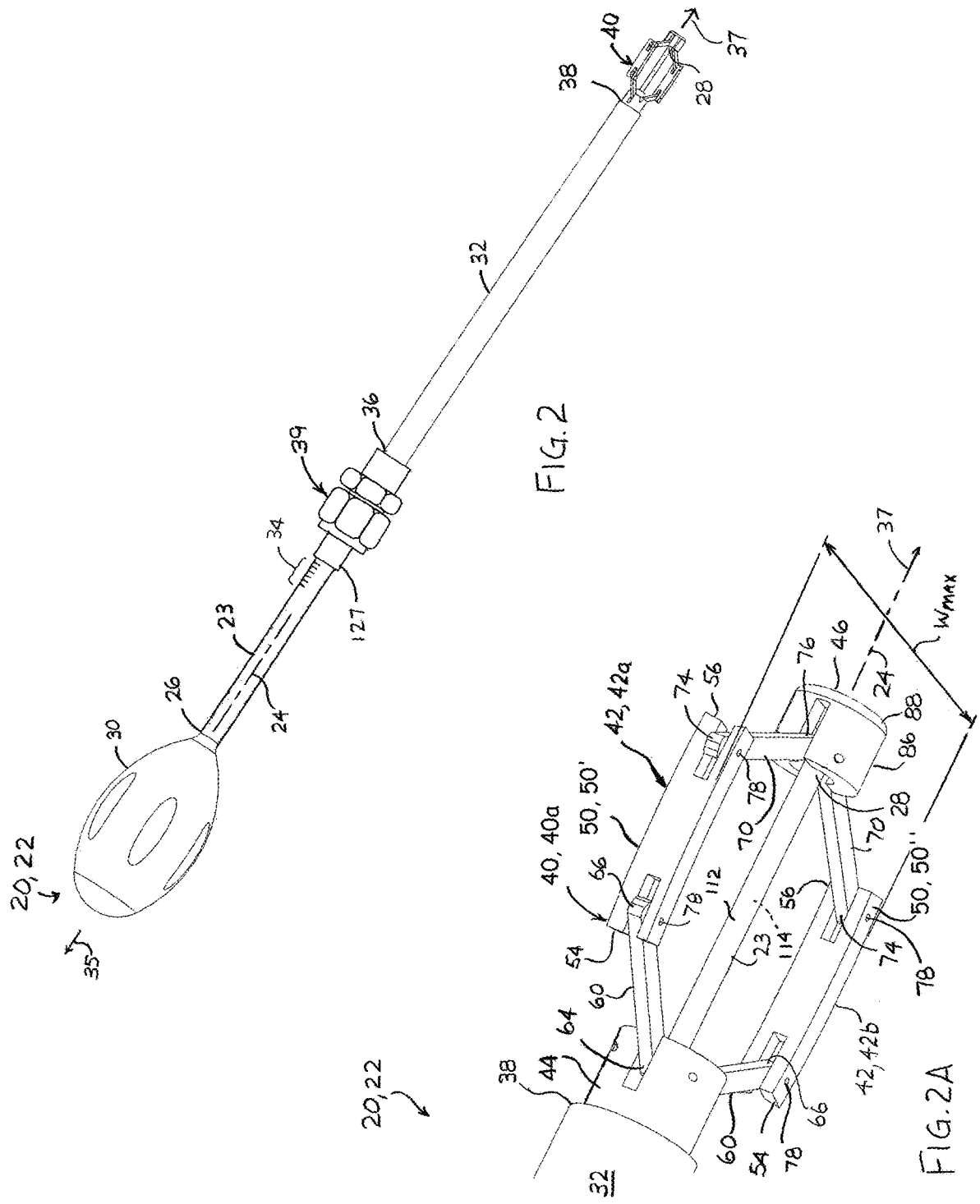
FIG. 2 is a perspective view of the lateral disc cutter of FIG. 1 in a fully extended configuration according to an embodiment of the disclosure.

Referring to FIGS. 1 and 2, a lateral disc cutter 20 for removing tissue between adjacent vertebrae of a spine is depicted in a fully retracted configuration 21 and a fully extended configuration 22, respectively, according to embodiments of the disclosure. The lateral disc cutter 20 includes a stem 23 that defines an actuation axis 24 and includes a proximal end 26 and a distal end 28. The proximal end 26 may be fitted with a knob or handle 30. The distal end 28 extends through a sleeve 32, the stem 23 being translatable within the sleeve 32 in a proximal direction 35 and a distal direction 37. In some embodiments, the stem 23 is also rotatable within the sleeve 32. The sleeve 32 includes a proximal end 36 and a distal end 38, and may include a stem lock assembly 39 affixed to the proximal end 36. In some embodiments, the stem 23 includes graduation lines 34 formed on a portion of the stem 23 that translates into and out of the sight tube 127 of the stem lock assembly 39 (or, when no stem lock assembly 39 is utilized, the proximal end 36 of the sleeve 32). A morcellator assembly 40 is affixed to the distal end 38 of the sleeve 32 and is coupled to the stem 23.

Referring to FIGS. 1A and 2A, a morcellator assembly 40a is depicted in greater detail. The morcellator assembly 40a includes at least one cutter assembly 42a pivotally mounted to a proximal collar or hub 44 and to a distal collar or hub 46. Each cutter assembly 42a includes a cutter or blade 50a having a proximal end 54 and a distal end 56, a proximal linkage 60 having a proximal end 64 and a distal end 66, and a distal linkage 70 having a proximal end 74 and a distal end 76. The proximal end 64 of the proximal linkage 60 is pivotally connected to the proximal hub 44. The distal end 66 of the proximal linkage 60 is pivotally connected the proximal end 54 of the blade 50a. The distal end 76 of the distal linkage 70 is pivotally connected to the distal hub 46, and the proximal end 74 of the distal linkage 70 is pivotally connected to the distal end 56 of the blade 50a. The pivotal connections may be accomplished, for example, by using hinge pins 78 that are affixed to the hubs 44, 46 and blade 50a, and about which the linkages 60 and 70 freely rotate (i.e., are "freely rotatable").

Herein, embodiments of the morcellator assemblies 40, cutter assemblies 42, and blades 50 are referred to collectively or generically with reference characters 40, 42, and 50 respectively. Individual or specific embodiments are referred to with reference characters 40, 42, and 50 followed by a letter suffix (e.g., "morcellator assembly 40a", "cutter assembly 42a", and "blade 50a").

The stem 23 and the proximal hub 44 are configured to enable translation of the stem 23 through the proximal hub 44. In some embodiments, the stem 23 is also rotatable within proximal hub 44. The distal end 28 of the stem 23 is captured within the distal hub 46, and may also be rotatable within the distal hub 46. In some embodiments, the distal end of the stem 23 includes or is fitted with a head portion 80 (FIG. 10). The head portion 80 may be oversized (depicted), undersized, or the same diameter as the stem 23, and may include a retention feature 82 (e.g., a flange) that is captured within a race 84 defined by the distal hub 46. The distal hub 46 may include a body portion 86 and an end cap 88 that cooperate to capture the head portion 80 within the distal hub 46.

The lateral disc cutter 20 is configured in the fully retracted configuration 21 (FIG. 1) by translating the stem 23 in the distal direction 37, until the cutter assembly 42, 42a is pulled taut in the distal direction 37. The translation of the stem 23 also translates the distal hub 46 away from the proximal hub 44, thereby elongating the cutter assembly or assemblies 42, 42a and drawing the blade 50, 50a radially inward, toward the actuation axis 24. The lateral disc cutter 20 is configured in the fully extended configuration 22 (FIG. 2) by translating the stem in the proximal direction 35 until the blades 50, 50a reach a maximum lateral displacement away from the actuation axis 24.

The translation of the stem 23 causes the graduation lines 34 to slide through a sight tube 127 of the stem lock assembly 39 (or alternatively, proximal end 36 of the sleeve 32) in succession. In some embodiments, each graduation line 34 includes a numerical label that corresponds to a displacement width W (e.g., in millimeters) of the morcellator assembly 40, 40a when the respective graduation line 34 is aligned with the proximal end 36 of the sleeve 32. This informs the operator what the cutting span of the morcellator assembly 40, 40a is at a given axial displacement of the stem 23 within the sleeve 32. Alternatively, the graduation lines 34 may include numerical labels that correspond to a length scale (e.g., millimeters), indicating the displacement of the stem 23 within the sleeve 32.

In some embodiments, when in the fully retracted configuration, the minimum displacement width WMIN of the morcellator assembly 40, 40a is in a range of 6 millimeters (mm) to 8 mm inclusive. In some embodiments, when in the fully extended configuration, the maximum displacement width WMAX of the morcellator assembly 40, 40a is in a range of 6 millimeters (mm) to 8 mm inclusive. Herein, a range that is said to be "inclusive" includes the stated endpoints of the range, as well as a values between the endpoints. Also herein, the displacement width "W" refers generically to any displacement width from WMIN to WMAX inclusive.

Figure 3:
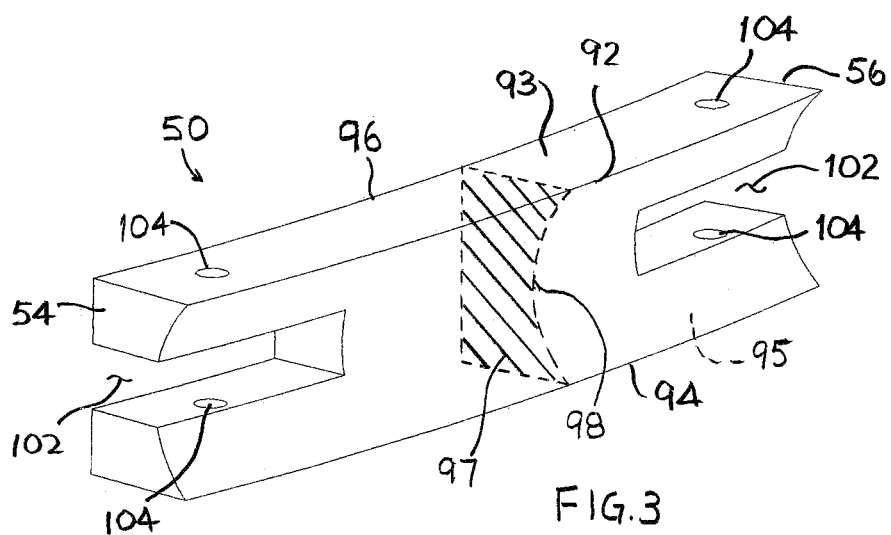
FIG. 3 is a perspective view of an arcuate cutting blade in isolation according to an embodiment of the disclosure.
Figure 4:
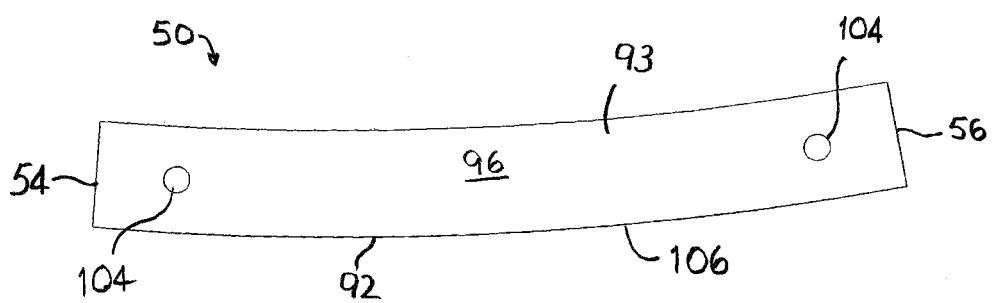
FIG. 4 is a plan view of the arcuate cutting blade of FIG. 3 according to an embodiment of the disclosure.

Referring to FIGS. 3 and 4, the blade 50a is depicted and described in more detail according to an embodiment of the disclosure. In the depicted embodiment, each blade 50a defines a first cutting edge 92 that borders a first surface 93 and extends from the proximal end 54 to the distal end 56 of the blade 50a, and a second cutting edge 94 that borders a second surface 95 that also extends from the proximal end 54 to the distal end 56 of the blade 50a, such that the first cutting edge 92 and the second cutting edge 94 extend in a direction that is substantially parallel to the actuation axis 24. In some embodiments, each of the blades 50a is an elongate, rigid block 96 having a cross-section 97 that defines a concave surface 98 between the first cutting edge 92 and the second cutting edge 94. The concave surface 98 may be arcuate, as depicted in FIG. 3. The concave surface 98 faces away from the actuation axis 24. The proximal and distal ends 54 and 56 of the blade 50a may each define a slot 102 that extends axially into the block 96 parallel to the first and second surfaces 93 and 95, and a mounting hole 104 that extends through the slot 102 and through the first and second surfaces 93 and 95. In some embodiments, the cutting edges 92 and 94 each define a convex profile 106 that bows laterally outward, away from the actuation axis 24. Alternatively, the profile of the cutting edges 92, 94 may be linear.

The morcellator assembly 40, 40a may include a single blade 50 and cutter assembly 42 or a plurality of blades 50 and cutter assemblies 42, such as a pair of blades 50' and 50" and cutter assemblies 42' and 42" depicted in the figures. In some embodiments, a first blade 50' of the pair of blades 50', 50" is disposed adjacent a first side 112 of the stem 23 and a second blade 50" of the pair of blades 50', 50" is disposed adjacent a second side 114 of the stem 23 (FIG. 2A). In some embodiments, the first side 112 and the second side 114 of the stem 23 are diametrically opposed. Other arrangements for a plurality of blades 50 are also contemplated, for example a three- or four-blade arrangement with the blades 50 distributed tangentially about the stem 23.

In assembly, the proximal hub 44 is affixed to the distal end 38 of the sleeve 32, for example by welding, crimping, pins, set screw, or threaded engagement. The proximal linkages 60 are pivotally coupled to the proximal hub 44 and the blades 50, and the distal linkages 70 pivotally coupled to the distal hub 46. With the end cap 88 removed, the distal end 28 of the stem 23 may be inserted into the proximal end 36 of the sleeve 32, through the distal end 38 of the sleeve 32, and through the hubs 44 and 46. For oversized head portions 80 (depicted), the head portion 80 can be removed during the insertion. With the distal end 28 of the stem 23 extending through the distal hub 46, the head portion 80 may be affixed to the distal end 28, the head portion 80 seated in the body portion 86 of the distal hub 46, and the end cap 88 secured to the body portion 86 to capture the head portion 80 and retention feature 82 within the distal hub 46. The handle 30 is affixed to the proximal end 26 of the stem 23.

Figure 5:
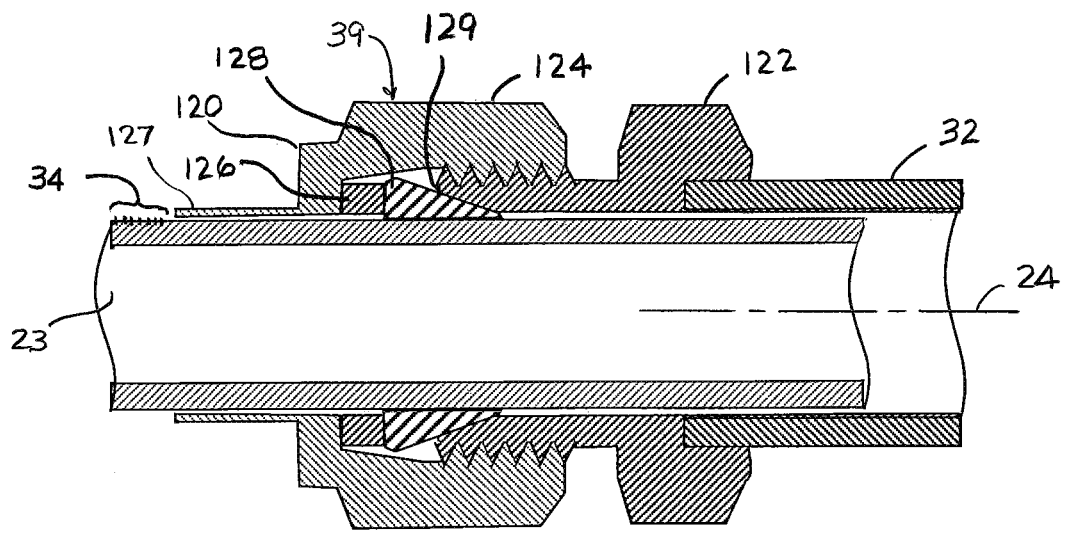
FIG. 5 is a sectional view a stem lock assembly of the lateral disc cutter of FIG. 1 according to an embodiment of the disclosure.

Referring to FIG. 5, the stem lock assembly 39 is depicted in greater detail according to an embodiment of the disclosure. In some embodiments, the stem lock assembly 39 includes a compression fitting 120 having a male threaded fitting 122, a cap nut 124, a slip ring 126, and a ferrule 128. The male threaded fitting 122 is affixed to the proximal end 36 of the sleeve 32, for example by welding, gluing, or a threaded coupling. The cap nut 124 threadably engages the male threaded fitting 122 and, when rotated, may slide over the slip ring 126. Tightening the cap nut 124 to the male threaded fitting 122 forces the ferrule 128 into a flared end 129 of the male threaded fitting 122, causing it to compress radially inward against the stem 23, thereby locking the stem 23 at an axial location within and relative to the sleeve 32. In some embodiments, the ferrule 128 is of a polymer material (e.g., NYLON), which yields under compression instead of dimpling of the stem 32. The stem lock assembly 39 may also include a sight tube 127 that protrudes proximally and aligns with the graduation lines 34 for easy reading of the displacement of the stem 23 relative to the sleeve 32 in operation. The depiction of FIG. 5 presents the male threaded fitting 122 and the cap nut 124 as having flats. It is understood that other external forms may be implemented for the male threaded fitting 122 and the cap nut, for example, a knurled cylinder.

Figure 6:
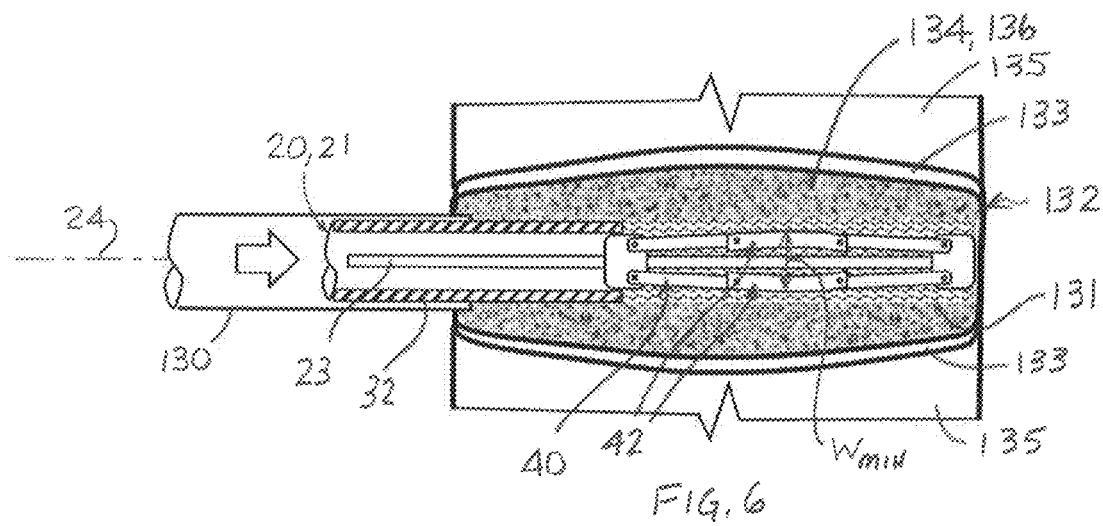
FIGS. 6 through 8 are lateral view schematics of a procedure for morcellating tissue in a disc nucleus with a lateral disc cutter of the present disclosure according to an embodiment of the disclosure.
Figure 7:
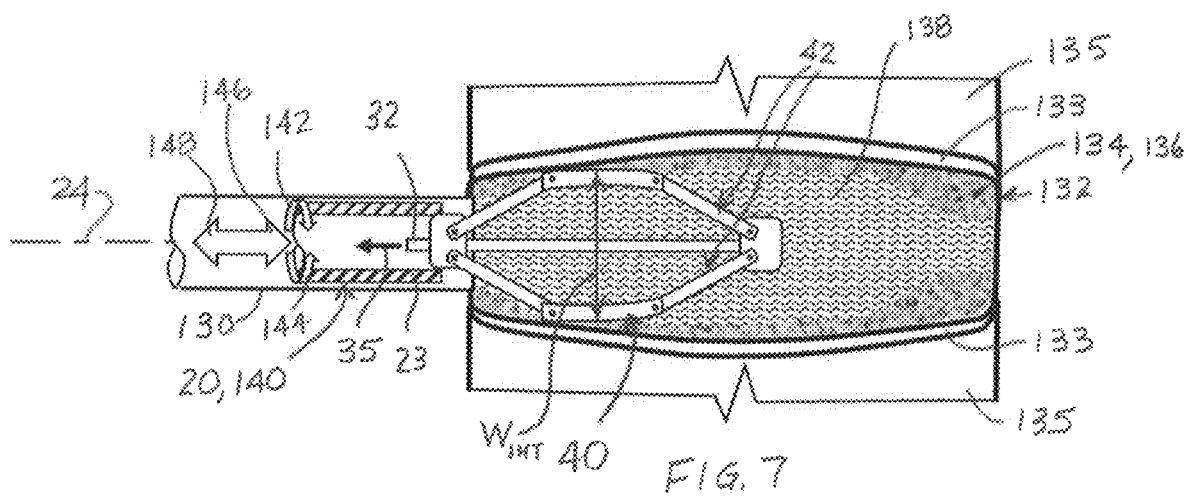
Figure 8:
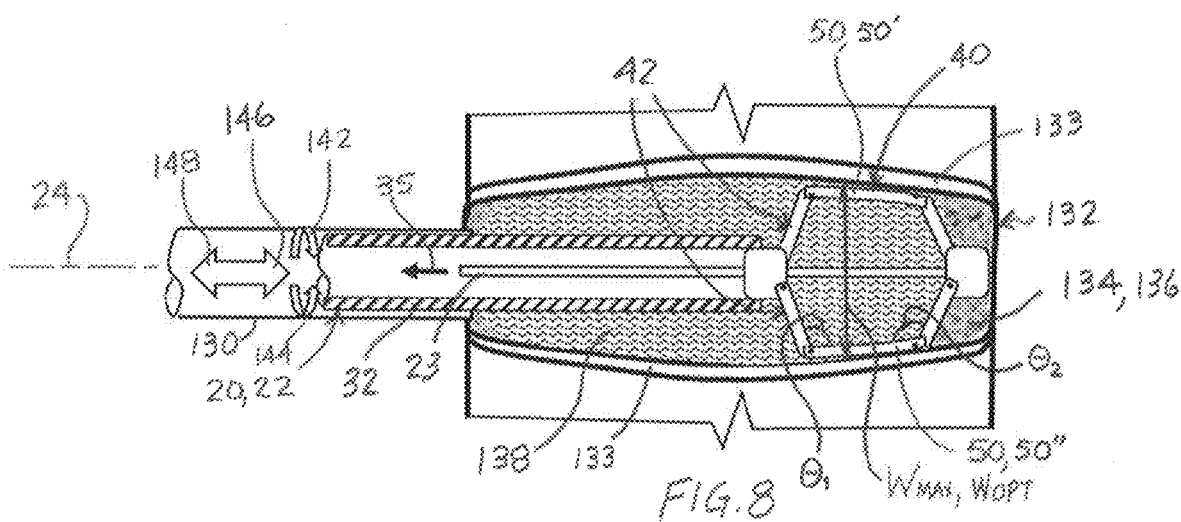

Referring to FIGS. 6 through 8, operation of the lateral disc cutter 20 is depicted according to an embodiment of the disclosure. Though FIGS. 6 through 8 depict the morcellator assembly 40a, cutter assembly 42a, and blade 50a, the operational description applies any of the morcellator assemblies 40, cutter assemblies 42, and blades 50 disclosed herein.

An access tube 130 is surgically inserted into an intervertebral disc 132 that is disposed between the endplates 133 of adjacent vertebrae 135, providing access to a nucleus 134 of the intervertebral disc 132. A core passage 131 is cut through the intervertebral disc 132 using standard tools and techniques available to the artisan, the core passage 131 having a diameter that approximates the inner diameter of the access tube 130. With the lateral disc cutter 20 in the fully retracted configuration 21, the lateral disc cutter 20 is inserted through the access tube 130 so that the morcellator assembly 40 extends into the core passage 131 (FIG. 6).

The morcellator assembly 40 may be configured in a partially extended configuration 140 (FIG. 7) by translating the stem 23 in the proximal direction 35, causing the cutter assembly 42 to flex outward and increase the displacement width W of the morcellator assembly 40. In the partially extended configuration 140, an intermediate displacement width WINT is attained that is between the values of WMIN in the fully retracted configuration 21 and WMAX in the fully extended configuration 22. For embodiments including the stem lock assembly 39, the stem lock assembly 39 may be set, which releasably fixes the stem 23 relative to the sleeve 32 and enables the lateral disc cutter 20 to be rotated as a unit by the handle 30 without altering or disturbing the displacement width W of the morcellator assembly 40. Securing the stem 23 relative to the sleeve 32 enables the lateral disc cutter 20 to be rotated about the actuation axis 24. Rotation of the lateral disc cutter 20 may be back and forth (i.e., alternating between clockwise and counterclockwise motion about the actuation axis 24) as represented by arrows 142 and 144.

In the partially extended configuration 140, the morcellator assembly 40 cuts into the core tissue 136 adjacent the core passage 131 to increase the region of morcellated tissue 138. The lateral disc cutter 20 may also be reciprocated fore and aft (i.e., in the generally posterior and anterior directions 146 and 148) within the disc nucleus 134 to further expand the region of morcellated tissue 138.

To increase the reach of the morcellator assembly 40 in the superior and inferior directions, the displacement width W of the morcellator assembly 40 is increased. The stem lock assembly 39 (when utilized) is released and the stem 32 translated in the proximal direction 35 until the desired displacement width W is attained. During this step, the graduation lines 134 may be used in conjunction with the sight tube 127 to inform the user of the displacement width W (e.g., FIG. 1). Upon reaching the desired displacement width W, the stem lock assembly 39 (when utilized) is reset and the process of rotating the lateral disc cutter 20 about the actuation axis 24 and, optionally, reciprocating the lateral disc cutter 20 in the posterior and anterior directions 146 and 148 is repeated, thereby increasing the region of morcellated tissue 138.

The process of releasing the stem lock assembly 39, expanding the morcellator assembly 40 and resetting the stem lock assembly 39, followed by rotation and reciprocation of the morcellator assembly 40 within the disc nucleus 134 is repeated until the morcellator assembly 40 reaches the fully extended configuration 22 (FIG. 8), or an optimum displacement width WOPT limited by the dimension between the adjacent vertebrae 135. When the displacement width WMAX or WOPT is such that the blades 50' and 50" contact the respective endplates 133 of the adjacent vertebrae 135, the morcellator assembly 40 may be used to cut through the outer tissue of the intervertebral disc 132 to scrape the bone tissue of the endplates 133. The convex profiles 106 of the blades 50 approximate the concave face of the endplates 133. Also, each cutter assembly 42 extends the respective blade 50 in an orientation that is generally parallel to a mid-plane of the intervertebral disc space, and providing contact with the respective endplate 133 that extends over a substantial portion of the blade 50. By this process, wide swaths of tissue at the boundary of the endplate 133 and the intervertebral disc 132 are decorticated from the intervertebral disc 132 and scraped off the endplates 133.

Once the morcellation and decortication is complete, the lateral disc cutter 20 is reconfigured in the fully retracted configuration 21 and withdrawn through the access tube 130. The morcellated tissue 138 may be withdrawn through the access tube 130, for example with a suction device.

Functionally, the fully retracted configuration 21 reduces the profile of the morcellator assembly to enable insertion through the access tube 130 in a minimally invasive surgical procedure. The tissue scraped from the endplates 133 may gather within the concavity provided by the concave surface during a scraping stroke. Also, the concave surface 98 of the blades 50 provide relief for the core tissue 136 as it is morcellated, preventing the cutting edges 92, 94 from fouling due to accumulation of compacted tissue. The relief provided by the concave surface 98 enables the tissue compressed by the rotational advancement of the surfaces 93 and 95 of the blades 50 during morcellation, to expand into the cavity defined by the concave surface 98 after being cut. This may inhibit fouling of the cutting edges 92, 94. The convex profiles 106 of the blades 50 may conform closely to the concave surfaces of the endplates 133 for morcellating tissue closer to the endplates 133. The convex profile 106 may also act as a lead-in that guides the morcellator assembly 40 back into the access tube 130 when withdrawing the lateral disc cutter 20.

A further aspect of the morcellator assembly 40 is the ability to conform to the endplates 133 by enabling the blades 50 to be arranged in a non-parallel orientation with respect to each other, which is illustrated in FIG. 8. In FIG. 8, the proximal linkages 60 define a first articulation angle θ1 with respect to each of the blades 50, while the distal linkages 70 define a second articulation angle θ2 with respect to each of the blades 50, where the first articulation angle θ1 is different from the second articulation angle θ2. The proximal linkages 60 may be generally free to pivot about the blade 50 and about the proximal hub 44 without restraint. Likewise, the distal linkages 70 may also be generally free to pivot about the blade 50 and about the distal hub 80 without restraint. Because of the free rotation, the blades 50 are able to better conform to the shape of the endplates 133 at the locality of contact.

Referring to FIGS. 9 and 10, a partial view of a lateral disc cutter 20a is depicted in the fully retracted configuration 21 and the fully extended configuration 22, respectively, according to embodiments of the disclosure. The lateral disc cutter 20a includes many of the same components and attributes as the lateral disc cutter 20, which are indicated with same-numbered reference characters. Only the distal portion of the lateral disc cutter 20a is portrayed in FIGS. 9 and 10. The proximal portion (not depicted) of the lateral disc cutter 20a may be of the same construction as the lateral disc cutter 20. Also in FIGS. 9 and 10, operation of the disc cutter 20a relative to the access tube 130 is depicted.

For the lateral disc cutter 20a, the stem 23 includes external thread 172 that define a threaded region 174 of the stem 23. The proximal hub 44 may include an internal thread 176 that are threadably engaged with the external thread 172 of the stem 23. In some embodiments, the stem 23 includes or is fitted with a stop 178 at a distal end 182 of the threaded region 174, the stop 178 being distal to the proximal hub 44. The stop 178 may be affixed to the stem 23 in a variety of ways available to the artisan, including threaded engagement (depicted), press fitting over an enlarged diameter portion of the stem 23, welding, with pins, with a set screw, or by gluing.

In operation, the lateral disc cutter 20a is pushed through the access tube 130 so that the morcellator assembly 40, 40a extends out of the distal end of the access tube 130. The external thread 172 of the stem 23 cooperates with the internal thread 176 of the proximal hub 44 for axially translating and positioning the stem 23 relative to the sleeve 32. For the lateral disc cutter 20a, the proximal hub 44, being affixed to the sleeve 32, remains stationary during rotation of the stem 23. During the rotation/translation of the stem 23, the head portion 80 and retention feature 82 are rotated within the distal hub 46 for the lateral disc cutter 20a.

Rotation of the stem 23 in a first rotational direction 184 causes the rotating stem 23 to translate in the proximal direction 35 which draws the distal hub 46 toward the proximal hub 44, thereby causing the proximal linkage 60 and the distal linkage 70 to pivot away from the stem 23 and translate the blade 50 away from the stem 23 and toward the fully extended configuration 22. When rotating the stem 23 in the first rotational direction 184, proximal translation of the stem 23 reaches a limit when the stop 178 engages a distal face of the proximal hub 44. In such embodiments, engagement of the stop 178 with the proximal hub 44 establishes the fully extended configuration 22.

Rotation of the stem 23 in a second rotational direction 186 that is opposite the first rotational direction 184 translates the distal hub 46 away from the proximal hub 44, thereby causing the proximal linkage 60 and the distal linkage 70 to pivot toward the stem 23 and translate the blade 50 toward the stem 23 and toward the fully retracted configuration 21. When rotating the stem 23 in the second rotational direction 186, distal translation of the stem 23 reaches a limit when the cutter assemblies 42, 42a are pulled taut between the proximal and distal hubs 44 and 46. For the lateral disc cutter 20a, the external thread 172 of the stem 23 extend through the proximal hub 44 when in the fully retracted configuration 21 and for all intermediate configurations between the fully retracted configuration 21 and the fully extended configuration 22.

Referring to FIG. 11, the stem 23 and blades 50 of the morcellator assembly 40a are depicted in cross-section according to an embodiment of the disclosure. The arrangement illustrates the concave surfaces 98 facing laterally away from the stem 23 and actuation axis 24.

Referring to FIGS. 12 and 13, a partial view of a lateral disc cutter 20b is depicted in the fully retracted configuration 21 and the fully extended configuration 22, respectively, according to embodiments of the disclosure. The lateral disc cutter 20b includes many of the same components and attributes as the lateral disc cutter 20a, which are indicated with same-numbered reference characters. Only the distal portion of the lateral disc cutter 20b is portrayed in FIGS. 12 and 13. The proximal portion of the lateral disc cutter 20b (not depicted) may be of the same construction as the lateral disc cutter 20. Also in FIGS. 12 and 13, the access tube 130 is depicted.

For the lateral disc cutter 20b, the external thread 172 of the stem 23 are disposed proximal to the proximal hub 44 and do not engage the proximal hub 44. Instead, a threaded insert 190 is disposed inside the sleeve 32 having internal threads 192 that engage the external thread 172. Also, the stop 178 may be disposed inside the sleeve 32 to engage the threaded insert 190 when the lateral disc cutter 20b is in the fully extended configuration 22. Accordingly, neither the external thread 172 nor the stop 178 extend outside the sleeve 32 during operation.

In assembly, the threaded insert 190 may be welded, glued, or crimped to the sleeve 32. Optionally, the threaded insert 190 may be manufactured as unitary with the sleeve 32. Optionally, the sleeve may be in multiple parts, with the threaded insert 190 including external threads to which the two parts are threadably engaged to form a joint at the threaded insert 190 (not depicted).

Referring to FIGS. 14 through 16, a morcellator assembly 40b is depicted according to an embodiment of the disclosure. The morcellator assembly 40b includes some of the same components and attributes as the morcellator assembly 40a, some of which are indicated with same-numbered reference characters. The morcellator assembly 40b may also be utilized with any of the lateral disc cutters 20 depicted herein. Distinctions of the morcellator assembly 40b include a cutter assembly 42b with blades 50b having blade end structures 202 and linkages 60 and 70 having linkage end structures 204, the blade end structures 202 and the linkage end structures 204 cooperating to define pivot joints 206 with structures that rotate about each other. For the cutter assembly 40b, each blade end structure 202 includes a spiral-shaped structure 212 that mates and cooperates with a hook-shaped structure 214 of the corresponding linkage end structure 204. Each of the pivot joints 206 define a pivot axis 216, and a baseline axis 218 of the blade 50b may be defined as extending through the pivot axes 216. Each linkage 60, 70 defines a linkage axis 220.

Referring to FIGS. 17 through 18A, the blade 50b is described in more detail according to an embodiment of the disclosure. The blade 50b may comprise an assembly 222 that includes containment portions 224 that extend perpendicular to the pivot axes 216. Each containment portion 224 extends along a respective side 226 of the spiral-shaped structure 212. In some embodiments, the containment portions 224 are fabricated separately and extend along a full length 228 of the assembly 222 (FIG. 18). In some embodiments, the containment portions 224 extend only partially along the length 228 of the assembly 222 (FIG. 18A). The containment portions 224 may be affixed to and integrated with the blade 50b, for example by a welding or brazing process. In some embodiments, the containment portion 224 defines the cutting edges 92, 94, with the concave surface 98 being defined by both the blade 50b and the containment portion(s) 224. In some embodiments, the concave surface 98 extends over a partial length 232 of the full length 228. The partial length 232 may be centered with respect to the full length 228. The blade 50b defines a thickness 238 of the spiral-shaped structure 212 that is parallel to the pivot axis 216. The blade 50b defines and is centered about a pivot plane 240 that is perpendicular to the pivot axes 216.

The containment structures 224 as depicted are separate structures that are integrated into the blade 50b. In some embodiments, one of the containment portions 224 may be unitary with the blade 50b (not depicted) and the other of the containment portions 224 provided as a separate structure for integration with the blade 50b. In such an embodiment, the spiral-shaped structure 212 may be end milled into the blade end structure 202, leaving a thickness of material that serves as the containment portion 224. The separately formed containment portion 224 is then affixed to the opposing side 226 of the blade 50b to contain the arcuate interior channel 254.

The containment portions 224 are depicted and described as plate-like structures that extend along the sides 226 of the blade 50b to cover the spiral-shaped structure 212. Alternatively, the containment portions 224 may be integrated with and extend along the sides of the hook-shaped structure 214. Other structures, such as pins or bars (not depicted) that extend along the sides of the spiral-shaped structure 212 or the hook-shaped structure 214 but do not entirely cover the spiral-shaped structure 212 are also contemplated. A forked arcuate end portion (not depicted) of the hook-shaped structure is also contemplated that straddles a pin (not depicted) that extends through the spiral-shaped structure 212 to bridge the arcuate interior channel 254 is also contemplated for containment of the hook-shaped structure 214 within the spiral-shaped structure 212.

Referring to FIG. 19, the blade end structure 202 for the cutter assembly 42b is depicted in greater detail according to an embodiment of the disclosure. For the cutter assembly 42b embodiment, the spiral-shaped structure 212 defines and extends along a spiral axis 242 and terminates at a detent 244, the detent 244 defining the pivot axis 216. The detent 244 may define a radius 246 that is centered about and extends partially around the pivot axis 216. The spiral-shaped structure 212 includes an interior surface 246 and an arcuate exterior surface 248 that merge at a spiral structure extremity 252 of the detent 244 at the spiral axis 242. The interior surface 246 defines an arcuate interior channel 254 that extends along and is centered about an arcuate interior axis 256. The arcuate interior axis 256 defines an axis radius 258 and a circular arc length 262 about the pivot axis 216, the circular arc length 262 defining a channel angle α about the pivot axis 216 that extends from the spiral structure extremity 252 of the detent 244 to an end socket 264 of the arcuate interior channel 254 at a channel extremity 266 that intersects the end socket 264 at the arcuate interior axis 256.

Referring to FIG. 202, the linkage end structure 204 for the cutter assembly 42b is depicted in greater detail according to an embodiment of the disclosure. For the cutter assembly 42b embodiment, the hook-shaped structure 214 includes a support portion 269 that transitions from the linkage 60, 70, a mid-portion 270 that extends from the support portion 269, and an arcuate end portion 272 that extends from the mid-portion 270. The mid-portion 270 and the arcuate end portion 272 define a recess 274. The arcuate end portion 272 defines and is centered about an end portion axis 276 and terminates at a free end 278. An end portion extremity 282 intersects the end portion axis 276 at the free end 278. The hook-shaped structure 214 also defines a gape 286 having a gape dimension 284, the gape dimension 284 being defined as a minimum distance between the free end 278 and a junction 288 of the mid-portion 270 and the support portion 269. The end portion axis 276 defines an end portion axis radius 290 that is substantially equal to the axis radius 258 of the spiral-shaped structure 202, the end portion axis 276 defining an end portion angle β that extends from the end portion extremity 282 of the arcuate end portion 272 to a junction 289 at the confluence of the arcuate end portion 272 and the mid portion 270. The end portion angle β may be equal to or greater than the channel angle α. The arcuate end portion 272 may be dimensioned for a close sliding fit within the arcuate interior channel 254 of the spiral-shaped structure 212.

Referring to FIG. 21, an example of the pivot joint 206 is depicted according to an embodiment of the disclosure. In some embodiments, the spiral-shaped structure 212 and the hook-shaped structure 214 each define the same thickness 238 that extends parallel to the pivot axis 216 (depicted). In some embodiments, the hook-shaped structure 214 defines a thickness that is slightly less than the thickness 238 of the spiral-shaped structure 212.

Referring to FIGS. 22A and 22B, a linkage end structure 204' for the cutter assembly 42b is depicted in an embodiment of the disclosure. The linkage end structure 204' includes at least some of the same components and attributes as the linkage end structure 204, some of which are indicated by same-numbered numerical references. The linkage end structure 204' also includes a shoulder portion 292 that transitions between the hook-shaped structure 214 and the linkage 60, 70, and is configured to register against the blade 50b in the fully extended configuration 22 depicted at FIG. 15. The shoulder portion 292 may be shaped to conform to the shape of the blade 50b along a contact interface 294 (FIG. 22B). For example, the shoulder portion 292 may define a concavity 296 that complements a convexity 298 of the blade 50b at the contact interface 294 (depicted). In some embodiments, the shoulder portion 292 is configured to engage the blade 50b when the free end 278 of the hook-shaped structure 214 is seated within the end socket 264 of the arcuate interior channel 254 of the spiral-shaped structure 212 (FIG. 22B).

Also depicted at FIGS. 22A and 22B are an in-line orientation 322 and a fully articulated orientation 324, respectively. In the in-line orientation 322, the baseline axis 218 of the blade 50b and the linkage axis 220 are substantially parallel, with the free end 278 of the hook-shaped structure 214 partially extending into the arcuate interior channel 254 of the spiral-shaped structure 212 and being separated from the end socket 264 of the arcuate interior channel 254 (FIG. 22A). The in-line orientation 322 may correspond to fully retracted configuration 21 of the lateral disc cutter 20, depicted at FIG. 14.

In the fully articulated orientation 324, the baseline axis 218 and the linkage axis 220 intersect at a minimum articulation angle θmin that is less than 180 degrees, with the free end 278 of the hook-shaped structure 214 extending into the arcuate interior channel 254 of the spiral-shaped structure 212 and being seated within the end socket 264 of the arcuate interior channel 254 (FIG. 22B). The fully articulated orientation 324 may correspond to the fully extended configuration 22 of the lateral disc cutter 20 depicted at FIG. 15. Though FIGS. 15 and 22B depict different magnitudes for the minimum articulation angle θmin, both are characterized by the free end 278 of the hook-shaped structure 214 being seated within the end socket 264 of the arcuate interior channel 254. Explanation of the differing magnitudes of θmin, is discussed attendant to FIGS. 24A and 24B.

Referring to FIGS. 23A through 23C, assembly of the blade 50b to the linkage 60, 70 is described according to an embodiment of the disclosure. The spiral-shaped structure 212 is positioned with the arcuate exterior surface 248 at the gape 286 of the recess 274. In some embodiments, the arcuate exterior surface 248 defines a dimension 302 parallel to the gape 286 that is greater than the gape dimension 284 (FIG. 23A). As the arcuate exterior surface 248 of the spiral-shaped structure 286 is pushed into the gape 286, the greater dimension 302 of the arcuate exterior surface 248 elastically deforms the hook-shaped structure 214, momentarily enlarging the gape dimension 284 to be equal to the dimension 302 and causing the arcuate end portion 272 to deflect (FIG. 23B). As the arcuate exterior surface 248 passes through the gape 286, resilience causes the arcuate end portion 272 of the hook-shaped structure 214 to snap back and partially around the detent 244, thereby securing the spiral-shaped structure 212 within the hook-shaped structure 214 (FIG. 23C). The blade 50b and the linkage 60, 70 may be arranged in the in-line orientation 322 to facilitate the assembly process (depicted).

Figure 24A:
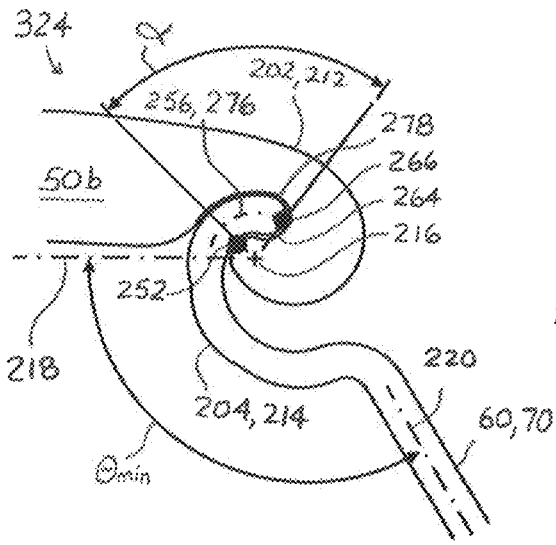
FIGS. 24A and 24B are plan views of pivot joints having spiral-shaped structures with different channel angles to define different minimum articulation angles according to embodiments of the disclosure.
Figure 24B:
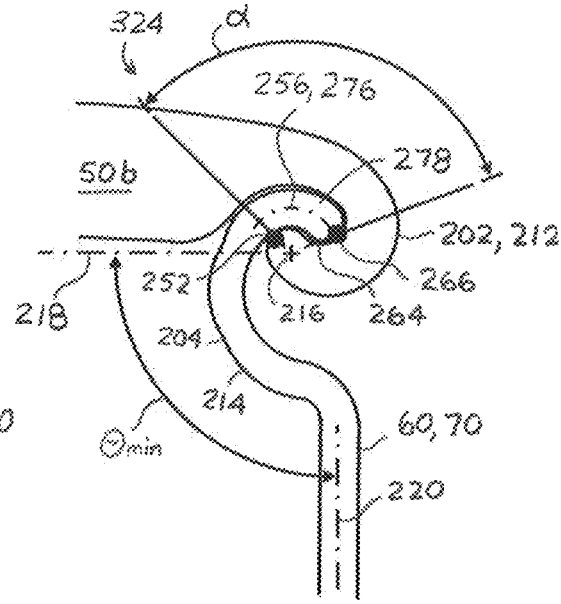

Referring to FIGS. 24A and 24B, the generally inverse relationship between the channel angle α and the minimum articulation angle θmin is depicted according to embodiments of the disclosure. For smaller channel angles α, the free end 278 of the hook-shaped structure 214 of the linkage end structure 204 engages the end socket 264 of the spiral-shaped structure 212 of the blade end structure 202 over a lesser rotational displacement from the in-line orientation 322, thereby defining a greater minimum articulation angle θmin (FIG. 24A). At greater channel angles α, the free end 278 of the hook-shaped structure 214 of the linkage end structure 204 engages the end socket 264 of the spiral-shaped structure 212 of the blade end structure 202 over a greater rotational displacement from the in-line orientation 322, thereby defining a smaller minimum articulation angle θmin (FIG. 24B).

Figure 25:
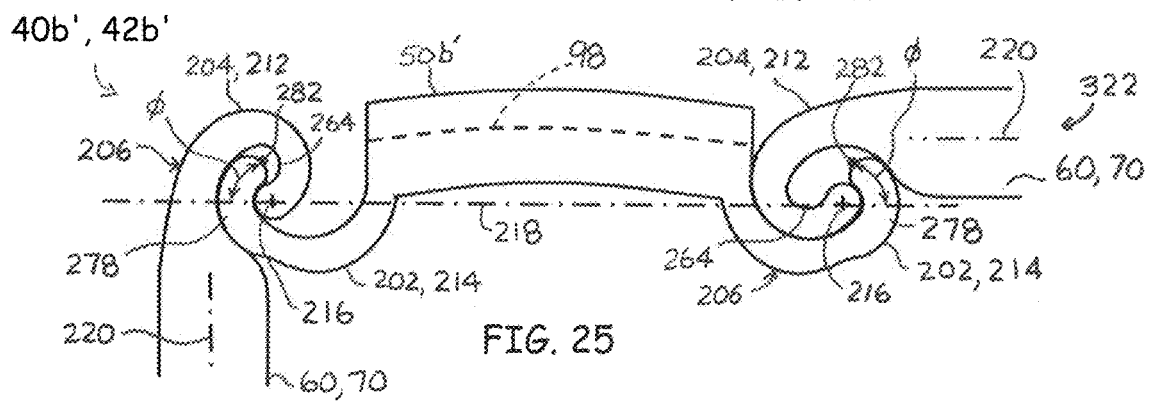
FIG. 25 is an enlarged, partial view of a cutter assembly with blades having hook-shaped structures according to an embodiment of the disclosure.

Referring to FIG. 25, a cutter assembly 42b' for use in a morcellator assembly 40b' is depicted according to an embodiment of the disclosure. The cutter assembly 42b' includes some of the same components and attributes as cutter assembly 42b, some of which are identified by same-numbered reference characters. For the cutter assembly 42b', a blade 50b' includes the hook-shaped structures 214 as the blade end structures 202 and the spiral-shaped structures 212 as the linkage end structures 204. For purposes of illustration, the linkage 60 is depicted in an intermediate orientation (i.e., between the in-line and the fully articulated configurations 322 and 324) and the linkage 70 in the in-line orientation 322. The hook-shaped structures 214 of the blade 50b' each define a stop angle ϕ that extends from the baseline axis 218 to the end portion extremity 282 about the pivot axis 216. In some embodiments, the stop angle ϕ is less than or equal to the end portion angle β of FIG. 20.

Figure 26A:
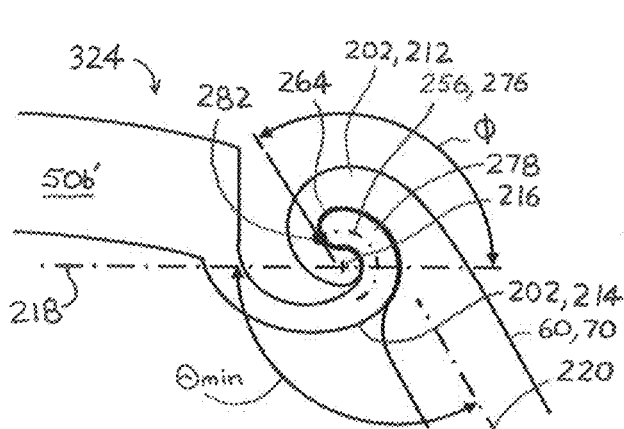
FIGS. 26A and 26B are plan views of pivot joints having hook-shaped structures with different stop angles for defining different minimum articulation angles according to embodiments of the disclosure.
Figure 26B:
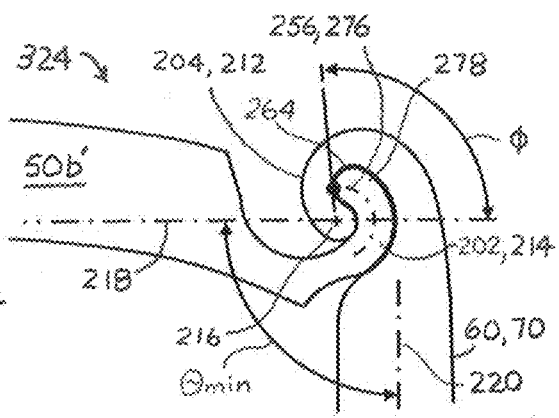

Referring to FIGS. 26A and 26B, the generally proportional relationship between the stop angle ϕ and the minimum articulation angle θmin for the blade 50b' is depicted according to embodiments of the disclosure. For greater stop angles ϕ, the free end 278 of the hook-shaped structure 214 of the blade end structure 202 engages the end socket 264 of the spiral-shaped structure 212 of the linkage end structures 214 over a lesser rotational displacement from the in-line orientation 322, thereby defining a greater minimum articulation angle θmin (FIG. 26A). At lesser stop angles ϕ, the free end 278 of the hook-shaped structure 214 of the blade end structure 202 engages the end socket 264 of the spiral-shaped structure 212 of the linkage end structures 214 over a greater rotational displacement from the in-line orientation 322, thereby defining a smaller minimum articulation angle θmin (FIG. 26B).

Functionally, articulation of the pivot joints 206 are provided by rotation of the arcuate end portion 272 of the hook-shaped structure 214 within the arcuate interior channel 254 of the spiral-shaped structure 212. The containment portions 224 capture the hook-shaped portion 214 within the spiral-shaped portion 212 during articulation. The close sliding fit between the arcuate end portion 272 and the arcuate interior channel 254 provides structural rigidity to the morcellator assembly 40b at intermediate orientations of articulation (i.e., at orientations where the articulation angles are greater than the minimum articulation angle θmin). When the pivot joint 206 reaches the fully articulated orientation 324, the free end 278 may be firmly seated within the end socket 264, further enhancing the strength and structural rigidity of the pivot joints 206. Furthermore, the shoulder portion 292 of the linkage end structure 204', when implemented, lends still greater structural rigidity to the morcellator assembly 40b at the fully articulated orientation 324. Accordingly, the structural rigidity of the morcellator assembly 40b is greatest in the fully extended configuration 22, when scraping against the vertebral endplate occurs.

During operation, the detents 244 serve the same function as the hinge pins 78 of blade 50a—that of providing a pivot between the blade 50b and the linkages 60 and 70. In some embodiments, the pivot joints 206 are "freely rotatable" at intermediate orientations of articulation as described attendant to FIG. 8, enabling the blades 50b to assume non-parallel orientations with respect to each other. The strength of the detent 244 is enhanced relative to a pin because it is supported by the arcuate end portion 272 along the length (thickness 238). Extending the concave surface 98 over the partial length 232 of the full length 228 of the blade 50a provides a compact profile for the blade 50b without encroaching on the material (and strength) of the spiral-shaped structures 212.

The arcuate end portion 272 of the hook-shaped structure 214 and the detent 244 of the spiral-shaped structure are said to "snappingly engage" when the arcuate exterior surface 248 of the spiral-shaped structure 212 is pushed through the gape 286 and captured within the recess 274 of the hook-shaped structure 214. The snapping engagement provides a tool-less way to couple and decouple the linkages 60, 70 and the blade 50b. Embodiments where the hook-shaped structure 214 defines a thickness that is slightly less than the thickness 238 of the spiral-shaped structure 212 provides clearance between the containment portions 224 for easier assembly, as well as easier articulation during operation.

The arcuate end portion 272 of the hook-shaped structure 214 remains captured within the arcuate interior channel 254 of the spiral-shaped structure 212 and between the containment portions 224 as the pivot joint 206 articulates between the in-line orientation 322 and the fully articulated orientation 324. In some embodiments, the stem 23 of the lateral disc cutter 20 limits the rotation of the cutter assembly 42b so that the hook-shaped structure 214 is prevented from rotating off the end of the spiral-shaped structure 212 (i.e., clockwise in FIG. 23C) when in the in-line orientation 322. An illustration of the stem 23 providing such rotational limitation is depicted in FIG. 14.

The above-described interactions between the spiral-shaped structures 212 and the hook-shaped structures 214 are the same for both FIG. 16 and FIG. 25. That is, whether the spiral-shaped structure 212 is the blade end structure 202 and the hook-shaped structure 214 is the linkage end structure 204, or vice-versa, the interactions between the blades 50 and the linkages 60, 70 are the same. The difference between utilizing the FIG. 16 and FIG. 25 embodiments is in the way the minimum articulation angle θmin and subsequent maximum displacement width WMAX the morcellator assembly 40 is established (FIG. 15). Inspection of FIG. 15 reveals that a maximum value of the maximum displacement width WMAX is realized for a minimum articulation angle θmin of 90 degrees. For the blades 50b, where the blade end structures 202 are the spiral-shaped structure 212, the channel angle α may be altered to affect the value of the minimum articulation angle θmin. For the blades 50b', where the blade end structures 202 are the hook-shaped structure 214, the stop angles π may be altered to affect the value of the minimum articulation angle θmin. By altering the blade end structures 202 (i.e., the channel angle α for blades 50b or the stop angles π for blades 50b'), the minimum articulation angle θmin can be altered to achieve a desired maximum displacement width WMAX without modification of the linkage end structures 204.

Figure 27A:
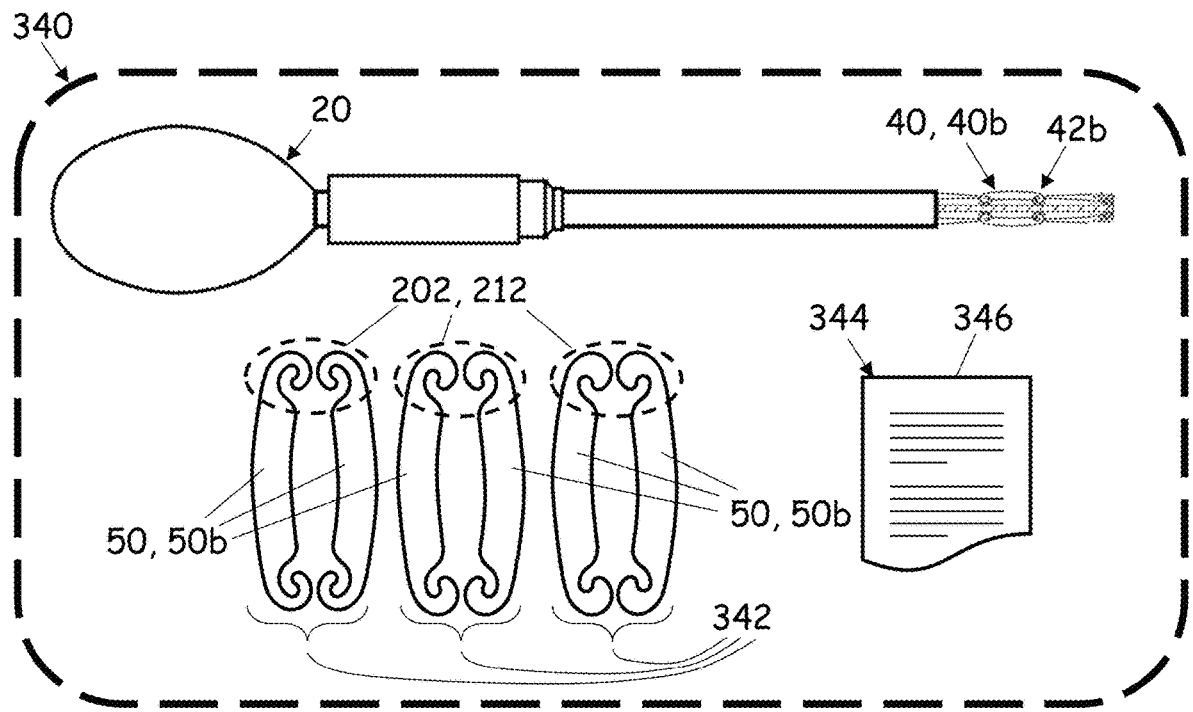
FIG. 27A is a schematic depiction of a kit having a plurality of blades with spiral-shaped structures defining different channel angles according to an embodiment of the disclosure.
Figure 27B:
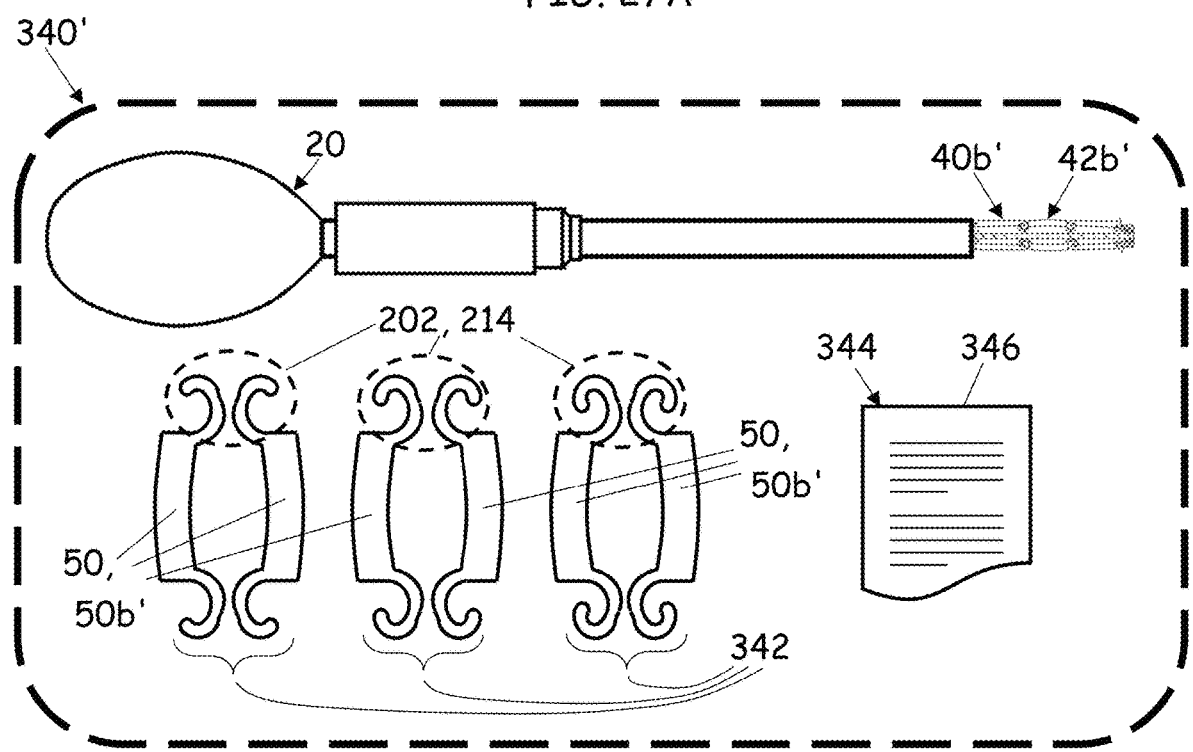
FIG. 27B is a schematic depiction of a kit having a plurality of blades with hook-shaped structures defining different stop angles according to an embodiment of the disclosure.

Referring to FIGS. 27A and 27B, kits 340 and 340' for establishing a plurality of values for the maximum displacement width WMAX are respectively depicted according to embodiments of the disclosure. Both kits 340 and 340' include a lateral disc cutter 20 having a morcellator assembly 40, a plurality of blade pairs 342, and a set of operating instructions 344. Each blade 50 of the blade pairs 342 are of identical construction.

The kits 340 and 340' differ in the form of the blade pairs 342 and morcellator assemblies 40. The kit 340 utilizes the morcellator assembly 40b of FIGS. 14 through 16 with cutter assemblies 42b. As such, the blades 50 blade pairs 342 of kit 340 comprise blades 50b having spiral-shaped structures 212 as the blade end structures 202, and the linkages 60, 70 have hook-shaped structures 214 as the linkage end structures 204. Each of the plurality of blades 50b have a unique circular arc length 262 and corresponding unique channel angle α as depicted and described at FIGS. 24A and 24B that, in turn, defines a unique minimum articulation angle θmin and corresponding WMAX as depicted and described at FIG. 15. In some embodiments, the maximum displacement width WMAX is predetermined for each blade pair 342 of the plurality of blades 50b.

The kit 340' utilizes the morcellator assembly 40b' of FIG. 25 with cutter assemblies 42b'. As such, the blades 50 of the blade pairs 342 of kit 340' comprise blades 50b' having hook-shaped structures 214 as the blade end structures 202, and the linkages 60, 70 have spiral-shaped structures 212 as the linkage end structures 204. Each blade 50b' of a given blade pair 342 define the stop angle φ that is unique to that blade pair 342, as depicted and described at FIGS. 26A and 26B. The unique stop angles φ, in turn, define a unique minimum articulation angle θmin and corresponding WMAX as depicted and described at FIG. 15. In some embodiments, the maximum displacement width WMAX is predetermined for each blade pair 342 of the plurality of blades 50b'.

The kits 340, 340' may be implemented in a method for assembling the morcellator assembly 40b, 40b'. In some embodiments, the method includes snapping the blade end and linkage end structures 202 and 204 together, for example as described attendant to FIGS. 23A through 23C. The blade 50b, 50b' and the linkage 60, 70 may be arranged in the in-line orientation 322 to facilitate the coupling of the blade end and linkage end structures 202 and 204. In some embodiments, the method includes selecting one of the plurality of blades 50b, 50b' for the step of snapping.

Functionally the method provides a way to selectively establish the maximum displacement width WMAX of the morcellator assembly 40. The method may be described in the operating instructions 344, and may be performed by a surgeon or other attendant during surgery without special tools for performing the method. The instructions may list a maximum lateral displacement width WMAX of the morcellator assembly 40b, 40b' associated for each of the plurality of blades 50b, 50b'.

In some embodiments, the operating instructions 344 are provided on tangible, non-transitory media 346. Non-limiting examples of tangible, non-transitory media 346 include a paper document (schematically depicted) or computer-readable media including compact disc and magnetic storage devices (e.g., hard disk, flash drive, cartridge, floppy drive). The computer-readable media may be local or accessible over the internet. The instructions 344 may be complete on a single medium, or divided among two or more media. For example, the kit 340, 340' may include some instructions 344 written on a paper document that instruct the operator to access one or more of the steps of the method over the internet, the internet-accessible steps being stored on a computer-readable medium or media. The instructions 344 may be in the form of written words, figures, and/or video or audio presentations. The method may be executed without the aid of instructions 344 or without providing the kit 340, 340'.

Figure 28:
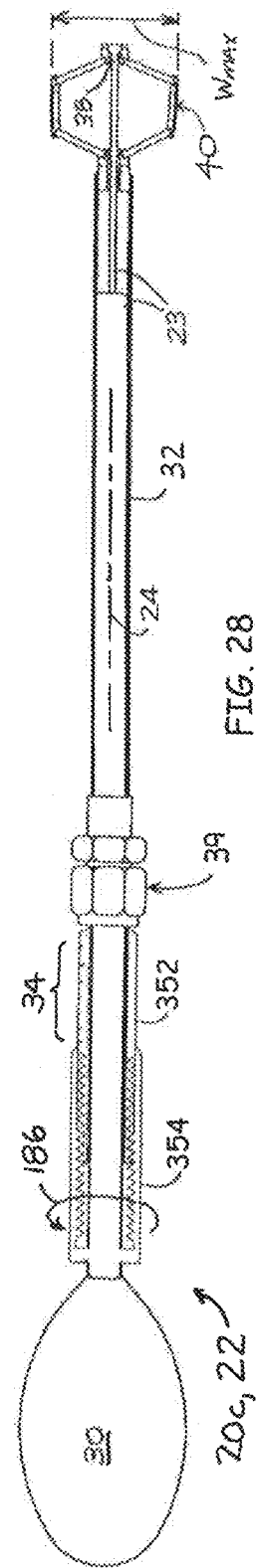
FIG. 28 is a sectional view of a screw driven lateral disc cutter with external drive threads at a proximal end and in an extended configuration according to an embodiment of the disclosure.
Figure 29:
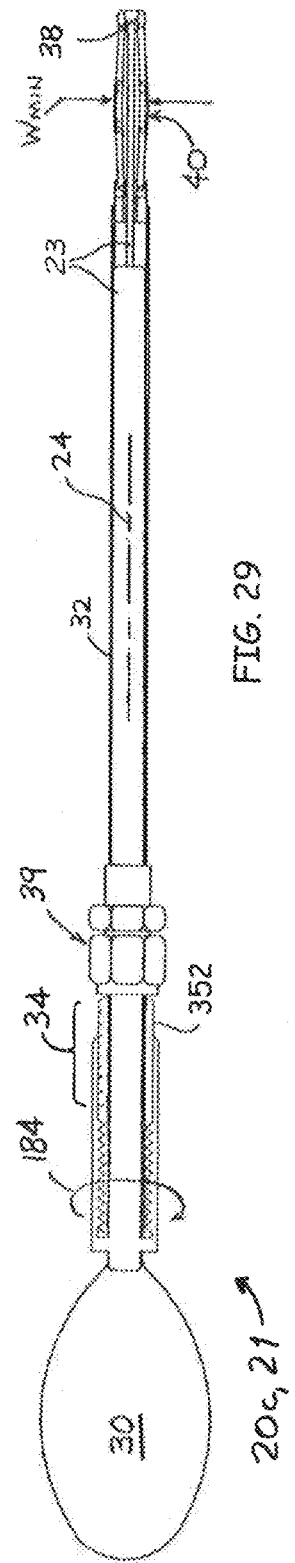
FIG. 29 is a sectional view of the screw driven lateral disc cutter of FIG. 28 in a retracted configuration according to an embodiment of the disclosure.
Figure 30:
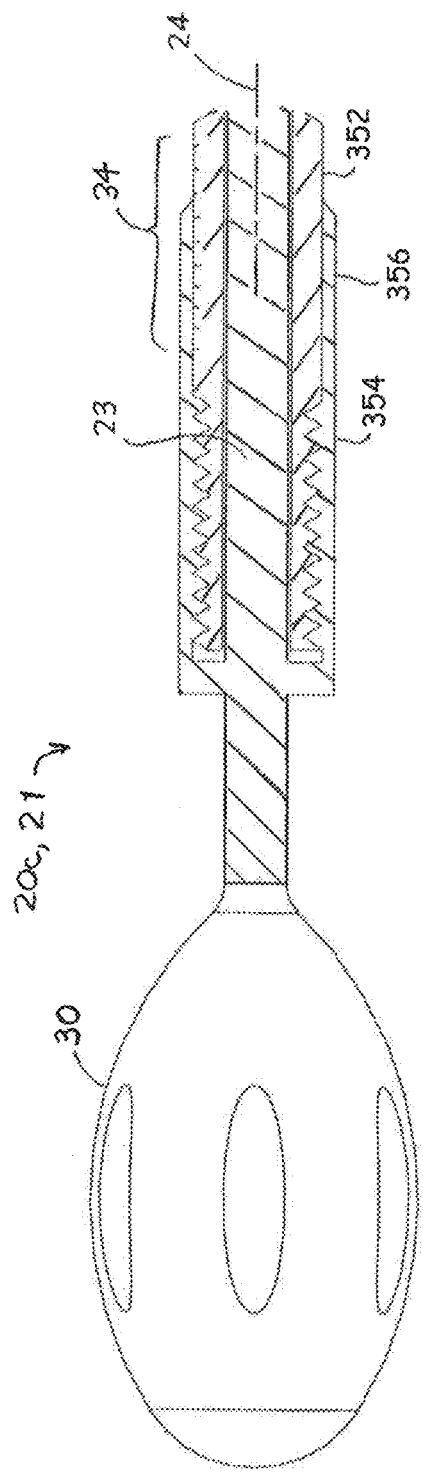
FIG. 30 is a partial sectional view of the proximal end of the lateral disc cutter of FIG. 29 in the fully extended configuration according to an embodiment of the disclosure.

Referring to FIGS. 28 through 30, a lateral disc cutter 20c is depicted in the fully extended configuration 22 and the fully retracted configuration 21, respectively, according to embodiments of the disclosure. The lateral disc cutter 20c includes many of the same components and attributes as the other lateral disc cutter 20a, some of which are indicated with same-numbered reference characters. The lateral disc cutter 20c includes a first threaded fitting 352 disposed at the proximal end of the stem lock assembly 39 that mates with a second threaded fitting 354 affixed to the stem 23 near the proximal end 26. Translation of the stem 23 relative to the sleeve 32 is accomplished by rotation of the stem 23 via handle 30, which adjusts and positions the second threaded fitting 354 axially along the first threaded fitting 352. The relative positioning of the threaded fittings 352, 354 positions the distal end 38 of the stem 23 for manipulating the morcellator assembly 40 and affecting a desired displacement width W. In some embodiments, the graduation lines 34 are disposed on the first threaded fitting 352, with the second threaded fitting 354 including a sight tube 356 that protrudes distally and aligns with the graduation lines 34 for easy reading of the displacement of the stem 23 relative to the sleeve 32 in operation.

In some embodiments, at least some of the operational steps of the lateral disc cutter 20 attendant to FIGS. 6 through 8 are provided as instructions that are provided along with any one of the lateral disc cutters 20, 20a, 20b, and 20c as a kit. Optionally, the access tube 130 may also be provided with the kit. Optionally, at least some of the operation of the screw driven lateral disc cutters 20a, 20b, and 20c may also be included with the instructions. The instructions are provided on a non-transitory medium, such as paper or a magnetic storage medium in computer readable format.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art. Herein, references to "proximal" and associated derivative terms refer to a direction or position that is toward the surgeon or operator. References to "distal" and associated derivative terms refer to a direction or position that is away from the surgeon or operator.

For purposes of interpreting the claims, it is expressly intended that the provisions of 35 U.S.C. 112(f) are not to be invoked unless the specific terms "means for" or "step for" are recited in the respective claim.

What is claimed is:

1. A surgical instrument for removing tissue between adjacent vertebrae of a spine, comprising:
a cutter assembly, including:
a blade including a blade end structure; and
a linkage including a linkage end structure that cooperates with said blade end structure to define a pivot joint for rotation of said linkage relative to said blade,
wherein:
one of said blade end structure and said linkage end structure includes a spiral-shaped structure that defines and extends along a spiral axis and terminates at a detent, said detent defining a pivot axis, said spiral-shaped structure including an interior surface and an exterior surface that merge at a spiral structure extremity of said detent at said spiral axis, said interior surface defining an arcuate interior channel that extends along and is centered about an arcuate interior axis, said arcuate interior axis defining an axis radius and a circular arc angle about said pivot axis, said circular arc length defining a channel angle about said pivot axis that extends from said spiral structure extremity of said detent to an end of said arcuate interior channel along said arcuate interior axis;
an other of said linkage end structure and said blade end structure includes a hook-shaped structure having an arcuate end portion that is centered about an end portion axis and terminates at an end portion extremity at said end portion axis, said end portion axis defining an end portion radius that is substantially equal to said axis radius, said end portion axis defining an end portion angle that is equal to or greater than said channel angle, said arcuate end portion being dimensioned for a close sliding fit within said arcuate interior channel.

2. The surgical instrument of claim 1, comprising a containment portion that extends perpendicular to said pivot axis along a side of said spiral-shaped structure for containment of said hook-shaped structure within said arcuate interior channel.

3. The surgical instrument of claim 2, wherein said containment portion is a separate structure that is affixed to said spiral-shaped structure.

4. The surgical instrument of claim 1, wherein said spiral-shaped structure and said hook-shaped structure define a thickness that is parallel to said pivot axis.

5. The surgical instrument of claim 1, wherein:
said blade defines a baseline axis and said linkage defines a linkage axis, said blade and said linkage being rotatable about said pivot axis in a pivot plane;
in an in-line orientation, said baseline axis and said linkage axis are substantially parallel, said end portion extremity being located within said arcuate interior channel and separated from said end of said arcuate interior channel;
in a fully articulated orientation, said baseline axis and said linkage axis intersect at a minimum articulation angle that is less than 180 degrees, said end portion extremity being located within said arcuate interior channel and registered against said end of said arcuate interior channel.

6. The surgical instrument of claim 5, wherein said end portion of said hook-shaped structure and said detent of said spiral-shaped structure are configured to snappingly engage when said blade and said linkage are in said in-line orientation.

7. The surgical instrument of claim 5, wherein said hook-shaped structure defines a recess that receives and captures said spiral-shaped structure when said blade and said linkage are in said in-line orientation.

8. The surgical instrument of claim 5, wherein said hook-shaped structure is adjacent a shoulder portion of said linkage that registers against said spiral-shaped structure when said blade and said linkage are in said fully articulated orientation.

9. The surgical instrument of claim 5, wherein registration of said end portion extremity against said end of said arcuate interior channel establishes a fully extended configuration of said surgical instrument.

10. The surgical instrument of claim 5, wherein said blade includes a second blade end structure and defines a concave surface that extends from a first cutting edge to a second cutting edge, said concave surface defining an axial length parallel to said baseline axis that is between said blade end structure and said second blade end structure.

11. The surgical instrument of claim 5, wherein said blade end structure includes said spiral-shaped structure.

12. The surgical instrument of claim 5, wherein a containment portion extends perpendicular to said pivot axis along a side of said spiral-shaped structure for containment of said hook-shaped structure within said arcuate interior channel, wherein said containment portion is a separate structure affixed to said blade and defines a cutting edge of said blade.

* * * * *